(12) United States Patent
Roudot et al.

(10) Patent No.: US 10,918,583 B2
(45) Date of Patent: *Feb. 16, 2021

(54) COSMETIC OR DERMATOLOGICAL COMPOSITION COMPRISING A MEROCYANINE, AN ORGANIC UVB-SCREENING AGENT AND AN ADDITIONAL ORGANIC UVA-SCREENING AGENT

(71) Applicant: L'OREAL, Paris (FR)

(72) Inventors: Angelina Roudot, Le Kremlin Bicêtre (FR); Didier Candau, Bievres (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/762,063

(22) PCT Filed: Jan. 20, 2014

(86) PCT No.: PCT/EP2014/051032
§ 371 (c)(1),
(2) Date: Jul. 20, 2015

(87) PCT Pub. No.: WO2014/111574
PCT Pub. Date: Jul. 24, 2014

(65) Prior Publication Data
US 2015/0366769 A1 Dec. 24, 2015

Related U.S. Application Data

(60) Provisional application No. 61/767,025, filed on Feb. 20, 2013, provisional application No. 61/767,304, (Continued)

(30) Foreign Application Priority Data

Jan. 21, 2013 (FR) .................. 13 50492
Jan. 21, 2013 (FR) .................. 13 50493
Jan. 21, 2013 (FR) .................. 13 50494

(51) Int. Cl.
| A61K 8/41 | (2006.01) |
| A61K 8/35 | (2006.01) |
| A61K 8/40 | (2006.01) |
| A61K 8/42 | (2006.01) |
| A61K 8/46 | (2006.01) |
| A61K 8/49 | (2006.01) |

(Continued)

(52) U.S. Cl.
CPC .................. *A61K 8/41* (2013.01); *A61K 8/06* (2013.01); *A61K 8/062* (2013.01); *A61K 8/35* (2013.01); *A61K 8/37* (2013.01); *A61K 8/40* (2013.01); *A61K 8/411* (2013.01); *A61K 8/42* (2013.01); *A61K 8/466* (2013.01); *A61K 8/4946* (2013.01); *A61K 8/4966* (2013.01); *A61K 8/585* (2013.01); *A61Q 17/04* (2013.01)

(58) Field of Classification Search
CPC . A61K 8/35; A61K 8/06; A61K 8/411; A61K 8/42; A61K 8/466; A61K 8/062; A61K 8/37; A61K 8/585; A61K 8/368; A61K 8/41; A61K 8/4946; A61K 8/4966; A61K 8/898; A61K 8/044; A61K 8/40; A61Q 17/04

See application file for complete search history.

(56) References Cited

U.S. PATENT DOCUMENTS

| 8,961,941 B2 * | 2/2015 | Richard ................... A61K 8/35 424/401 |
| 2008/0124285 A1 * | 5/2008 | Wagner .................... A61K 8/41 424/59 |
| 2013/0142737 A1 * | 6/2013 | Schlifkeposchalko ...................... C07D 249/20 424/59 |

FOREIGN PATENT DOCUMENTS

| CN | 101711151 A | 5/2010 |
| WO | WO-2008/090066 A2 | 7/2008 |

(Continued)

*Primary Examiner* — Blessing M Fubara
(74) *Attorney, Agent, or Firm* — Polsinelli PC

(57) ABSTRACT

The present invention relates to a cosmetic or dermatological composition comprising, in a physiologically acceptable support: a) at least one oily phase and b) at least one merocyanine compound of formula (1) defined hereinbelow and c) at least one organic UVB-screening agent chosen from: v) a liquid lipophilic organic UVB-screening agent vi) a hydrophilic organic UVB-screening agent vii) a triazine UVB-screening agent and viii) mixtures thereof; and d) at least one organic UVA-screening agent other than the said merocyanine compound; when the said UVB-screening agent is liquid and lipophilic, the said composition contains less than 2% by weight of cyclohexasiloxane relative to the total weight of the composition. Another subject of the present invention consists of a non-therapeutic cosmetic process for caring for and/or making up a keratin material, comprising the application, to the surface of the said keratin material, of at least one composition according to the invention as defined above. The invention also relates to a non-therapeutic cosmetic process for limiting the darkening of the skin and/or improving the colour and/or uniformity of the complexion, comprising the application, to the surface of the keratin material, of at least one composition as defined previously. The invention also relates to a non-therapeutic cosmetic process for preventing and/or treating the signs of ageing of a keratin material, comprising the application, to the surface of the keratin material, of at least one composition as defined previously.

30 Claims, No Drawings

Related U.S. Application Data filed on Feb. 21, 2013, provisional application No. 61/767,354, filed on Feb. 21, 2013.

(51) Int. Cl.
  *A61Q 17/04* (2006.01)
  *A61K 8/06* (2006.01)
  *A61K 8/37* (2006.01)
  *A61K 8/58* (2006.01)

(56) References Cited

FOREIGN PATENT DOCUMENTS

WO  WO 2013/011094 A2 *  1/2013
WO  WO 2013/011480 A1    1/2013

* cited by examiner

COSMETIC OR DERMATOLOGICAL COMPOSITION COMPRISING A MEROCYANINE, AN ORGANIC UVB-SCREENING AGENT AND AN ADDITIONAL ORGANIC UVA-SCREENING AGENT

CROSS REFERENCE TO RELATED APPLICATIONS

This application is a National Phase filing under 35 U.S.C. § 371 of PCT/EP2014/051032 filed on Jan. 20, 2014; and this application claims priority to Application No. 1350492 filed in France on Jan. 21, 2013, Application No. 1350493 filed in France on Jan. 21, 2013 and Application No. 1350494 filed in France on Jan. 21, 2013; and this application claims the benefit of U.S. Provisional Application No. 61/767,025 filed on Feb. 20, 2013, U.S. Provisional Application No. 61/767,304 filed on Feb. 21, 2013 and U.S. Provisional Application No. 61/767,354 filed on Feb. 21, 2013. The entire contents of each application are hereby incorporated by reference.

The present invention relates to a cosmetic or dermatological composition comprising, in a physiologically acceptable support:
  a) at least one oily phase and
  b) at least one merocyanine compound of formula (1) defined hereinbelow and
  c) at least one organic UVB-screening agent chosen from:
    i) a liquid lipophilic organic UVB-screening agent
    ii) a hydrophilic organic UVB-screening agent
    iii) a triazine UVB-screening agent and
    iv) mixtures thereof; and
  d) at least one organic UVA-screening agent other than the said merocyanine compound;
when the said UVB-screening agent is liquid and lipophilic, the said composition contains less than 2% by weight of cyclohexasiloxane relative to the total weight of the composition.

Another subject of the present invention consists of a non-therapeutic cosmetic process for caring for and/or making up a keratin material, comprising the application, to the surface of the said keratin material, of at least one composition according to the invention as defined above.

The invention also relates to a non-therapeutic cosmetic process for limiting the darkening of the skin and/or improving the colour and/or the uniformity of the complexion, comprising the application, to the surface of the keratin material, of at least one composition as defined previously.

The invention also relates to a non-therapeutic cosmetic process for preventing and/or treating the signs of ageing of a keratin material, comprising the application, to the surface of the keratin material, of at least one composition as defined previously.

It is known that radiation with wavelengths of between 280 nm and 400 nm permits tanning of the human epidermis and that radiation with wavelengths of between 280 and 320 nm, known as UV-B rays, harms the development of a natural tan. Exposure is also liable to bring about a detrimental change in the biomechanical properties of the epidermis, which is reflected by the appearance of wrinkles, leading to premature ageing of the skin.

It is also known that UV-A rays with wavelengths of between 320 and 400 nm penetrate more deeply into the skin than UV-B rays. UV-A rays cause immediate and persistent browning of the skin. Daily exposure to UVA rays, even of short duration, under normal conditions can result in damage to the collagen fibres and the elastin, which is reflected by a modification in the microrelief of the skin, the appearance of wrinkles and uneven pigmentation (liver spots, lack of uniformity of the complexion).

Protection against UVA and UVB rays is thus necessary. An efficient photoprotective product should protect against both UVA and UVB rays.

Many photoprotective compositions have been proposed to date to overcome the effects induced by UVA and/or UVB rays. They generally contain organic and/or mineral UV-screening agents, which function according to their own chemical nature and according to their own properties by absorption, reflection or scattering of the UV rays. They generally contain mixtures of liposoluble organic screening agents and/or of water-soluble UV-screening agents combined with metal oxide pigments such as titanium dioxide or zinc oxide.

Many cosmetic compositions for limiting the darkening of the skin and improving the colour and uniformity of the complexion have been proposed to date. It is well known in the field of antisun products that such compositions may be obtained by using UV-screening agents, and in particular UVB-screening agents. Certain compositions may also contain UVA-screening agents. This screening system should cover UVB protection for the purpose of limiting and controlling the neosynthesis of melanin, which promotes the overall pigmentation, but should also cover UVA protection so as to limit and control the oxidation of the already-existing melanin leading to darkening of the skin colour.

However, it is extremely difficult to find a composition which contains a particular combination of UV-screening agents that would be especially suited to improving the quality of the skin as regards both the colour and its mechanical elasticity properties. This improvement is particularly sought on already-pigmented skin so as not to increase the melanin pigmentary load or the structure of the melanin already present in the skin.

In point of fact, the majority of the organic UV-screening agents consist of aromatic compounds which absorb in the wavelength range between 280 and 370 nm. In addition to their power for screening out sunlight, the desired photoprotective compounds should also have good cosmetic properties, good solubility in the usual solvents and in particular in fatty substances such as oils, and also good chemical stability and good photostability alone or in combination with other UV-screening agents. They should also be colourless or at least have a colour that is cosmetically acceptable to the consumer.

One of the main drawbacks known to date of these antisun compositions is that their systems for screening out UVA and UVB radiation are insufficiently effective against UV rays and in particular against long UVA rays with wavelengths beyond 370 nm, for the purpose of controlling photo-induced pigmentation and its evolution by means of a system for screening out UV over the entire UV spectrum.

Liquid lipophilic organic UVB-screening agents are particularly advantageous since they do not require solvents to dissolve them in the oils usually used in antisun compositions. These liquid UVB-screening agents are mainly chosen from β,β-diphenylacrylate compounds such as Octocrylene, salicylate compounds such as Homosalate and ethylhexyl salicylate, and cinnamate compounds such as ethylhexyl methoxycinnamate.

The UVA and UVB screening systems containing these liquid organic UVB-screening agents combined with commonly-used organic UVA-screening agents do not, however, afford broad UV protection over the range 280 to 400 nm.

Hydrophilic organic UVB-screening agents are particularly advantageous since they can be dissolved in the aqueous phase and thus limit the amount of oils usually used in antisun compositions. Among the commonly-used hydrophilic UVB-screening agents, mention may be made of phenylbenzimidazole compounds, such as phenylbenzimidazolesulfonic acid sold especially under the trade name Eusolex 232 by Merck.

The UVA and UVB screening systems containing these hydrophilic organic UVB-screening agents combined with commonly-used organic UVA-screening agents do not, however, afford broad UV protection over the range 280 to 400 nm.

Triazine UVB-screening agents are particularly advantageous for their satisfactory UVB-ray-absorbing properties. They are described in patents U.S. Pat. No. 4,724,137, EP 0 517 104, EP 0 570 838, EP 0 796 851 and EP 0 775 698. Products that are particularly known include the derivative 2,4,6-tris[p-(2'-ethylhexyl-1'-oxycarbonyl)anilino]-1,3,5-triazine, which is sold especially under the trade name Uvinul T 150 by the company BASF, and 2-[(p-(tert-butylamido)anilino]-4,6-bis[(p-(2'-ethylhexyl-1'-oxycarbonyl)anilino]-1,3,5-triazine or Diethylhexyl Butamido Triazone (INCI name), sold under the trade name Uvasorb HEB by Sigma 3V.

The UVA and UVB screening systems containing these UVB-screening triazines combined with commonly-used organic UVA-screening agents do not, however, Merocyanine compounds are known in patent U.S. Pat. No. 4,195,999, patent application WO2004/006878, patent applications WO2008/090066, WO2011/113718, WO2009/027258, WO2013010590, WO2013/011094, WO2013/011480 and the documents IP COM JOURNAL No 000179675D published on Feb. 23, 2009, IP COM JOURNAL No 000182396D published on April 29, IP COM JOURNAL No 000189542D published on Nov. 12, 2009, IP COM Journal No IPCOM000011179D published on Mar. 4, 2004.

Some of these compounds may show the following drawbacks:
relatively unsatisfactory solubility in the usual solvents and in particular in fatty substances such as oils which may require a laborious formulation process and/or may result in cosmetic drawbacks such as a greasy effect on application;
an unsatisfactory chemical stability and/or unsatisfactory photostability;
produce a color liable to discourage the consumer from using a cosmetic or dermatological composition containing them.

The UVA and UVB screening systems consisting of (1) some of these merocyanine screening agents as the compound Octyl-5-N,N-diethylamino-2-phenysulfonyl-2,4-pentadienoate corresponding to the compound MC172 of structure

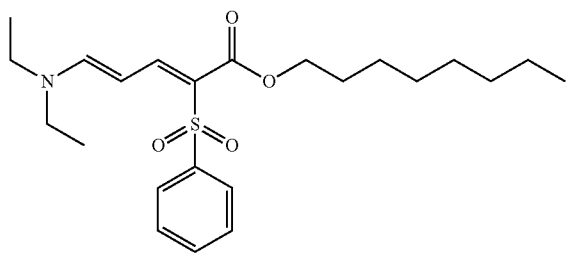 [SMILES: CCCCCCCCOC(=O)/C(=C/C=C/N(CC)CC)S(=O)(=O)c1ccccc1]

(2) at least one organic liquid lipophilic UVB filter and/or one organic hydrophilic UVB filter and/or one triazine UVB filter and (3) of at least one commonly used organic UVA filter do not always make it possible to afford broad UV protection over the range 280 to 400 nm and especially to obtain an observable absorbance up to a wavelength of 400 nm inclusive.

There thus remains a need to find a novel UVA and UVB screening system based on (1) at least one merocyanine compound, (2) at least one UVB-screening agent that is one organic liquid lipophilic UVB filter and/or one organic hydrophilic UVB filter and/or one UVB filter of the triazine type and at least one organic UVA filter, which is photostable and which ensures overall protection against UV rays from 280 to 400 nm especially having notable absorbance ranging up to a wavelength of 400 nm inclusive, in a manner that is stable over time and at high temperatures, without the drawbacks as previously defined.

The Applicant has found, surprisingly, that this objective can be achieved by using a) at least one organic liquid lipophilic UVB filter and/or at least one organic hydrophilic UVB filter and/or at least one UVB triazine filter, b) a particular merocyanine of formula (1) which will be defined in detail herein below and c) at least one organic UVA filter other than the said merocyanine.

Furthermore, the merocyanine compounds of formula (1) herein below, present surprisingly the advantage to be significantly less colored than the merocyanine compounds as disclosed in the application WO2008/090066 as the compound MC11 also called MC03 in the application WO2009/027258.

Those discoveries form the basis of the present invention.

Thus, in accordance with one of the objects of the present invention, a cosmetic or dermatological composition is now proposed, comprising, in a physiologically acceptable support:
a) at least one oily phase and
b) at least one merocyanine compound of formula (1) defined hereinbelow and
c) at least one organic UVB-screening agent chosen from:
i) a liquid lipophilic organic UVB-screening agent
ii) a hydrophilic organic UVB-screening agent
iii) a triazine UVB-screening agent and
iv) mixtures thereof; and
d) at least one organic UVA-screening agent other than the said merocyanine compound;
when the said UVB-screening agent is liquid and lipophilic, the said composition contains less than 2% by weight of cyclohexasiloxane relative to the total weight of the composition.

Another subject of the present invention consists of a non-therapeutic cosmetic process for caring for and/or making up a keratin material, comprising the application, to the surface of the said keratin material, of at least one composition according to the invention as defined above.

The invention also relates to a non-therapeutic cosmetic process for limiting the darkening of the skin and/or improving the colour and/or the uniformity of the complexion, comprising the application, to the surface of the keratin material, of at least one composition as defined previously.

The invention also relates to a non-therapeutic cosmetic process for preventing and/or treating the signs of ageing of a keratin material, comprising the application, to the surface of the keratin material, of at least one composition as defined previously.

Other characteristics, aspects and advantages of the invention will emerge on reading the detailed description that follows.

The expression "human keratin materials" means the skin (body, face, area around the eyes), hair, eyelashes, eyebrows, body hair, nails, lips or mucous membranes.

The term "physiologically acceptable" means compatible with the skin and/or its integuments, having a pleasant colour, odour and feel and not causing any unacceptable discomfort (stinging, tautness or redness) liable to discourage the consumer from using this composition.

The term "liquid lipophilic organic UVB-screening agent" means any organic chemical molecule that is capable of absorbing at least UVB rays in the wavelength range between 280 and 320 nm; the said molecule being in liquid form at room temperature (20-25° C.) and at atmospheric pressure (760 mmHg) and capable of being completely dissolved in molecular form in a liquid fatty phase or of being dissolved in colloidal form (for example in micellar form) in a liquid fatty phase.

The term "hydrophilic organic UVB-screening agent" means any organic chemical molecule that is capable of absorbing at least UVB rays in the wavelength range between 280 and 320 nm; the said molecule being capable of being completely dissolved in molecular form in an aqueous phase or of being dissolved in colloidal form (for example in micellar form) in an aqueous phase.

The term "organic UVA-screening agent" means any organic chemical molecule that is capable of absorbing at least UVA rays in the wavelength range between 320 and 400 nm; the said molecule also being able to absorb UVB rays in the wavelength range between 280 and 320 nm.

The term "between X and Y" means the range of values also including the limits X and Y.

According to the invention, the term "preventing" or "prevention" means reducing the risk of occurrence or slowing down the occurrence of a given phenomenon, namely, according to the present invention, the signs of ageing of a keratin material.

Merocyanines

According to the present invention, the merocyanine compounds in accordance with the invention correspond to formula (1) below, and also the E/E- or E/Z-geometrical isomer forms thereof:

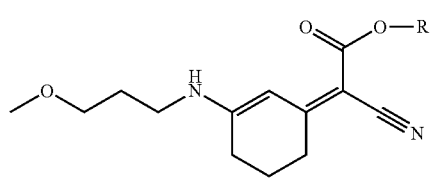

(1)

in which:

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, the said groups possibly being substituted with one or more O.

The merocyanine compounds of the invention may be in their E/E- or E/Z-geometrical isomer forms.

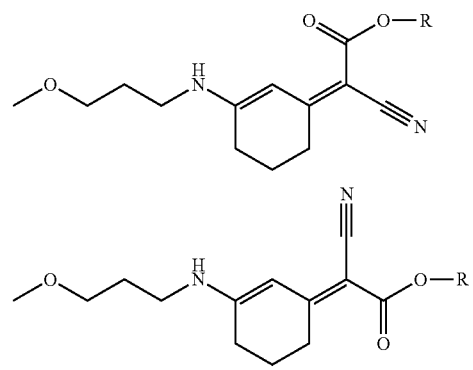

The preferential compounds of formula (1) are those in which:

R is a $C_1$-$C_{22}$ alkyl, which may be interrupted with one or more O.

Among the compounds of formula (1), use will be made more particularly of those chosen from the following compounds, and also the E/E- or E/Z-geometrical isomer forms thereof:

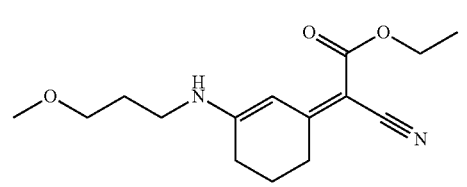

1 ethyl (2Z)-cyanol{3-[(3-methoxypropyl)amino]cyclohex-2-en-1-ylidene}ethanoate

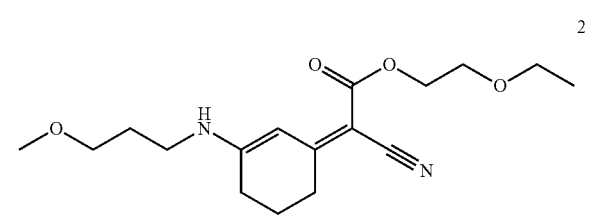

2

2-ethoxyethyl (2Z)-cyanol{3-[(3-methoxypropyl)amino]cyclohex-2-en-1-ylidene}ethanoate

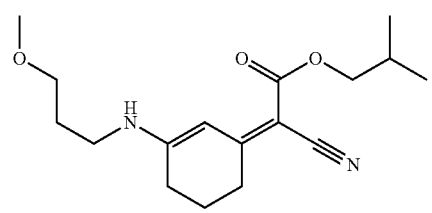

3

2-methylpropyl (2Z)-cyanol{3-[(3-methoxypropyl)amino]cyclohex-2-en-1-ylidene}ethanoate -continued

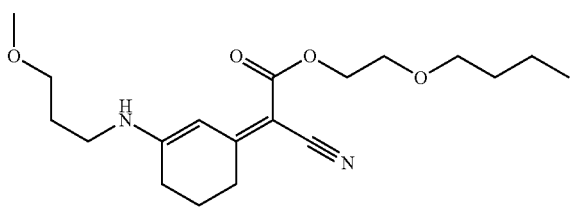

2-butoxyethyl (2Z)-cyanol{3-[(3-methoxypropyl)amino]cyclohex-2-en-1-ylidene}ethanoate

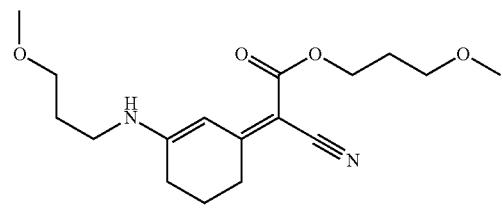

3-methoxypropyl (2Z)-cyanol{3-[(3-methoxypropyl)amino]cyclohex-2-en-1-ylidene}ethanoate

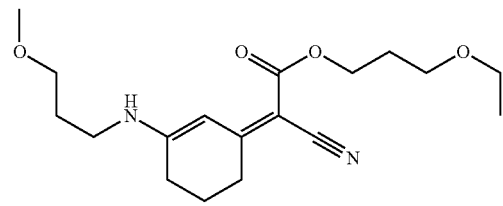

3-ethoxypropyl (2Z)-cyanol{3-[(3-methoxypropyl)amino]cyclohex-2-en-1-ylidene}ethanoate According to a particular mode of the invention, use will be made of those chosen from the following compounds, and also the E/E- or E/Z-geometrical isomer forms thereof:

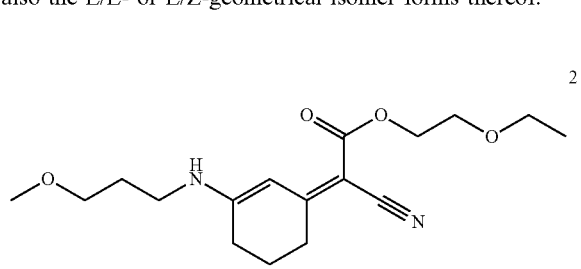

2-ethoxyethyl (2Z)-cyanol{3-[(3-methoxypropyl)amino]cyclohex-2-en-1-ylidene}ethanoate

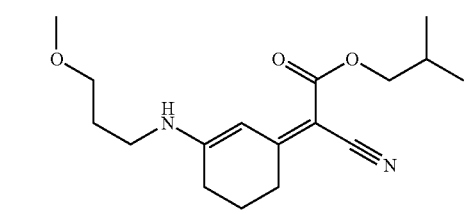

2-methylpropyl (2Z)-cyanol{3-[(3-methoxypropyl)amino]cyclohex-2-en-1-ylidene}ethanoate -continued

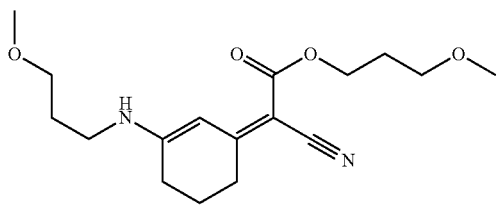

2-butoxyethyl (2Z)-cyanol{3-[(3-methoxypropyl)amino]cyclohex-2-en-1-ylidene}ethanoate

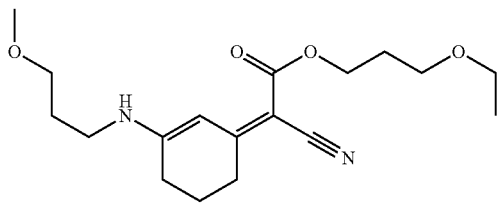

3-methoxypropyl (2Z)-cyanol{3-[(3-methoxypropyl)amino]cyclohex-2-en-1-ylidene}ethanoate 3-ethoxypropyl (2Z)-cyanol{3-[(3-methoxypropyl)amino]cyclohex-2-en-1-ylidene}ethanoate According to a more particularly preferred mode of the invention, use will be made of the compound 2-ethoxyethyl (2Z)-cyano{3-[(3-methoxypropyl)amino]cyclohex-2-en-1-ylidene}ethanoate (2) in its E/Z geometrical configuration having the following structure:

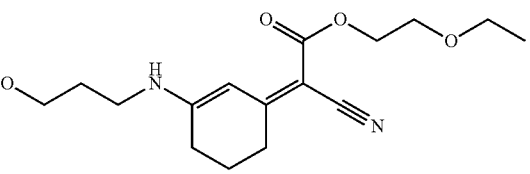

and/or in its E/E geometrical configuration having the following structure:

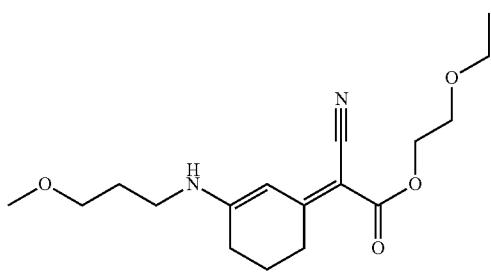 [SMILES: CCOCCOC(=O)/C(C#N)=C1/C=C(NCCCOC)CCC1]

The merocyanines of formula (1) according to the invention are preferably present in the compositions according to the invention in a concentration ranging from 0.1% to 10% by weight and preferentially from 0.2% to 5% by weight relative to the total weight of the composition.

The compounds of formula (1) may be prepared according to the protocols described in Pat. Appl. WO 2007/071 582, in IP.com Journal (2009), 9(5A), 29-30 IPCOM000182396D under the title "Process for producing 3-amino-2-cyclohexan-1-ylidene compounds" and in U.S. Pat. No. 4,749,643 on column 13, line 66—column 14, line 57 and the references cited in this regard.

Liquid Lipophilic Organic UVB-Screening Agents

The liquid organic UVB-screening agents that may be used according to the invention are preferably chosen from:
  liquid lipophilic β,β-diphenylacrylate compounds
  liquid lipophilic salicylate compounds
  liquid lipophilic cinnamate compounds
  and mixtures thereof.

a) β,β-Diphenylacrylate Compounds

Among the organic liquid lipophilic UVB-screening agents that may be used according to the invention, mention may be made of the liquid lipophilic alkyl β,β-diphenylacrylate or α-cyano-β,β-diphenylacrylate compounds of formula (I) below:

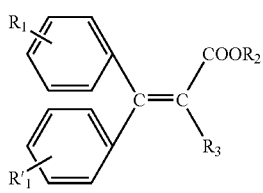

in which $R_1$ to $R_3$ may take the following meanings:
  $R_1$ and $R'_1$, which may be identical or different, represent a hydrogen atom, a straight or branched chain $C_1$-$C_8$ alkoxy radical or a straight or branched chain $C_1$-$C_4$ alkyl radical,
  $R_1$ and $R'_1$ being in the meta or para position;
  $R_2$ represents a straight or branched chain $C_1$-$C_{12}$ alkyl radical;
  $R_3$ represents a hydrogen atom or a CN radical.

Among the straight or branched chain $C_1$-$C_8$ alkoxy radicals, examples that may be mentioned include methoxy, ethoxy, n-propoxy, isopropoxy, n-butoxy, isobutoxy, tert-butoxy, n-amyloxy, isoamyloxy, neopentyloxy, n-hexyloxy, n-heptyloxy, n-octyloxy and 2-ethylhexyloxy radicals.

Among the straight or branched chain $C_1$-$C_4$ alkyl radicals, mention may be made more particularly of methyl, ethyl, n-propyl, isopropyl, n-butyl, isobutyl and tert-butyl radicals. Among the $C_1$-$C_{12}$ alkyl radicals, examples that may be mentioned, in addition to those mentioned above, include n-amyl, isoamyl, neopentyl, n-hexyl, n-heptyl, n-octyl, 2-ethylhexyl, decyl and lauryl radicals.

Among the compounds of general formula (I), the following compounds are more particularly preferred:
  2-ethylhexyl α-cyano-3,3-diphenylacrylate,
  ethyl α-cyano-β,β-diphenylacrylate, such as Etocrylene sold especially under the trade name Uvinul N35® by BASF,
  2-ethylhexyl β,β-diphenylacrylate,
  ethyl β,β-bis(4'methoxyphenyl)acrylate.

Among the compounds of general formula (I), the compound 2-ethylhexyl 2-cyano-3,3-diphenylacrylate, or Octocrylene, sold especially under the trade name Uvinul N539 by BASF, is even more particularly preferred.

b) Salicylate Compounds

Among the liquid lipophilic salicylate compounds that may be used according to the invention, mention may be made of:
  Homosalate sold under the name Eusolex HMS by Rona/EM Industries,
  Ethylhexyl salicylate sold under the name Neo Heliopan OS by Symrise, c) Cinnamate Compounds Among the liquid lipophilic cinnamate compounds that may be used according to the invention, mention may be made of:
  Ethylhexyl methoxycinnamate sold especially under the trade name Parsol MCX by DSM Nutritional Products,
  Isopropyl methoxycinnamate,
  Isoamyl methoxycinnamate sold under the trade name Neo Heliopan E 1000 by Symrise.

Among the liquid lipophilic UVB-screening agents according to the invention, use will be made more particularly of the compounds chosen from:
  Octocrylene
  Homosalate,
  Ethylhexyl salicylate
  Ethylhexyl methoxycinnamate, and mixtures thereof.

Among these liquid lipophilic UVB-screening agents, use will be made more preferentially of the compounds chosen from:
  Octocrylene
  Ethylhexyl salicylate, and mixtures thereof, and even more particularly Octocrylene.

The liquid lipophilic UVB-screening agent(s) according to the invention are preferably present in the compositions according to the invention in a concentration ranging from 0.1% to 40% by weight, preferentially from 0.2% to 25% by weight and even more preferentially from 0.5% to 15% by weight relative to the total weight of the composition.

Hydrophilic Organic UVB-Screening Agents

The hydrophilic organic UVB-screening agents are especially chosen from:
  hydrophilic cinnamic derivatives such as ferulic acid or 3-methoxy-4-hydroxycinnamic acid;
  hydrophilic benzylidenecamphor compounds;
  hydrophilic phenylbenzimidazole compounds;
  hydrophilic p-aminobenzoic (PABA) compounds;
  hydrophilic salicylic compounds;
  and mixtures thereof.

As examples of hydrophilic organic UVB-screening agents, mention may be made of those denoted hereinbelow under their INCI name:

Para-Aminobenzoic Compounds:
  PABA,

PEG-25 PABA, sold under the name Uvinul P 25® by BASF.

Salicylic Compounds:

Dipropylene Glycol Salicylate, sold under the name Dipsal® by Scher, TEA Salicylate, sold under the name Neo Heliopan TS® by Symrise.

Benzylidenecamphor Compounds:

Benzylidene Camphor Sulfonic Acid, manufactured under the name Mexoryl SL® by Chimex, Camphor Benzalkonium Methosulfate, manufactured under the name Mexoryl SO® by Chimex.

Phenylbenzimidazole Compounds:

Phenylbenzimidazole Sulfonic Acid, sold in particular under the trade name Eusolex 232® by Merck.

Use will be made more particularly of the screening agent Phenylbenzimidazole Sulfonic Acid, sold especially under the trade name Eusolex 232® by Merck.

The hydrophilic UVB-screening agent(s) may be present in the compositions according to the invention in contents ranging from 0.1% to 15% by weight and preferably ranging from 0.2% to 10% by weight relative to the total weight of the composition.

Triazine UVB-Screening Agent

Among the triazine UVB-screening agents in accordance with the invention, mention may be made of the 1,3,5-triazine derivatives of formula (I) below

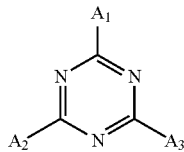
(I)

in which the radicals $A_1$, $A_2$ and $A_3$, which may be identical or different, are chosen from the groups of formula (II):

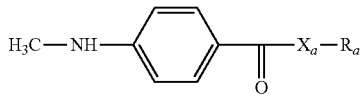
(II)

in which:
  $X_a$, which may be identical or different, represent oxygen or an —NH— radical;
  $R_a$, which may be identical or different, are chosen from a linear or branched $C_1$-$C_{18}$ alkyl radical; a $C_5$-$C_{12}$ cycloalkyl radical optionally substituted with one or more $C_1$-$C_4$ alkyl radicals; a polyoxyethylene radical comprising from 1 to 6 ethylene oxide units and in which the end OH group is methylated; a radical of formula (III), (IV) or (V) below:

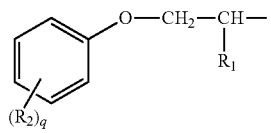
(III)

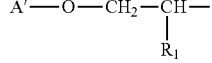
(IV)

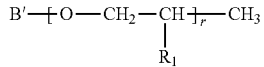
(V)

in which:
  $R_1$ is hydrogen or a methyl radical;
  $R_2$ is a $C_1$-$C_9$ alkyl radical;
  q is an integer ranging from 0 to 3;
  r is an integer ranging from 1 to 10;
  A' is a $C_4$-$C_8$ alkyl radical or a $C_5$-$C_8$ cycloalkyl radical;
  B' is chosen from: a linear or branched $C_1$-$C_8$ alkyl radical; a $C_5$-$C_8$ cycloalkyl radical; an aryl radical optionally substituted with one or more $C_1$-$C_4$ alkyl radicals.

it being understood that when $A_1$, $A_2$ and $A_3$ are identical and $X_a$ denotes an oxygen atom, then $R_a$ represents a branched $C_6$-$C_{18}$ alkyl radical.

A first more particularly preferred family of 1,3,5-triazine derivatives of formula (I) is that described especially in document EP-A-0 517 104, which corresponds to the 1,3,5-triazines of formula (I) in which $A_1$, $A_2$ and $A_3$ are of formula (II) and have the following characteristics:
  one or two radicals $X_a$—$R_a$ represents the radical —NH—$R_a$ with $R_a$ chosen from: a $C_5$-$C_{12}$ cycloalkyl radical optionally substituted with one or more $C_1$-$C_4$ alkyl radicals; a radical of formula (III), (IV) or (V) above in which:
  B' is a $C_1$-$C_4$ alkyl radical;
  $R_2$ is a methyl radical;
  the other two $X_a$—$R_a$ represent a radical —O—$R_a$ with $R_a$, which may be identical or different, chosen from: hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a radical of formula (III), (IV) or (V) above in which:
  B' is a $C_1$-$C_4$ alkyl radical;
  $R_2$ is a methyl radical.

A second more particularly preferred family of compounds of formula (I) is that consisting of 1,3,5-triazine derivatives described in document EP-A-0 570 838, which corresponds to the 1,3,5-triazines of formula (I) in which $A_1$, $A_2$ and $A_3$ are of formula (II) and have all of the following characteristics:
  one or two radicals $X_a$—$R_a$ represents the radical —NH—$R_a$ with $R_a$ chosen from: a linear or branched $C_1$-$C_{18}$ alkyl radical; a $C_5$-$C_{12}$ cycloalkyl radical optionally substituted with one or more $C_1$-$C_4$ alkyl radicals; a radical of formula (III), (IV) or (V) above in which:
  B' is a $C_1$-$C_4$ alkyl radical;
  $R_2$ is a methyl radical;
  the other or the other two $X_a$—$R_a$ being the radical —O—$R_a$ with $R_a$, which may be identical or different, chosen from: hydrogen; an alkali metal; an ammonium radical optionally substituted with one or more alkyl or hydroxyalkyl radicals; a linear or branched $C_1$-$C_{18}$ alkyl radical; a $C_5$-$C_{12}$ cycloalkyl radical optionally substituted with one or more $C_1$-$C_4$ alkyl radicals; a radical of formula (III), (IV) or (V) above in which:
  B' is a $C_1$-$C_4$ alkyl radical;
  $R_2$ is a methyl radical.

A third preferred family of compounds of formula (I) that may be used in the context of the present invention, and which is especially described in document U.S. Pat. No. 4,724,137, which corresponds to the 1,3,5-triazines of formula (I) in which $A_1$, $A_2$ and $A_3$ are of formula (II) and have the following characteristics:

$X_a$ are identical and represent oxygen;

$R_a$, which may be identical or different, represent a $C_6$-$C_{12}$ alkyl radical or a polyoxyalkylene radical comprising from 1 to 6 ethylene oxide units and in which the end OH group is methylated.

Among the triazine UVB compounds of formula (I), the following will more particularly be chosen:

2-[(p-(tert-butylamido)anilino]-4,6-bis[(p-(2'-ethylhexyl-1'-oxycarbonyl)anilino]-1,3,5-triazine or Diethylhexyl Butamido Triazone sold under the trade name Uvasorb HEB by Sigma 3V and corresponding to the following formula:

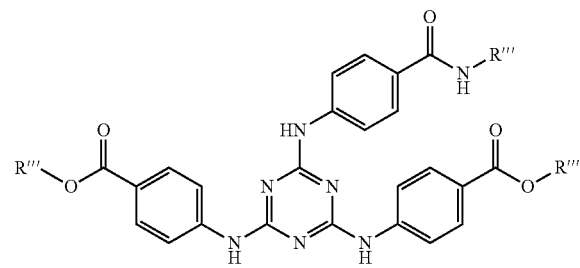

in which R''' denotes a 2-ethylhexyl radical and R'' denotes a tert-butyl radical;

2,4,6-tris[p-(2'-ethylhexyl-1'-oxycarbonyl)anilino]-1,3,5-triazine or Ethylhexyl Triazone sold especially under the trade name Uvinul T 150 by the company BASF and corresponding to the following formula:

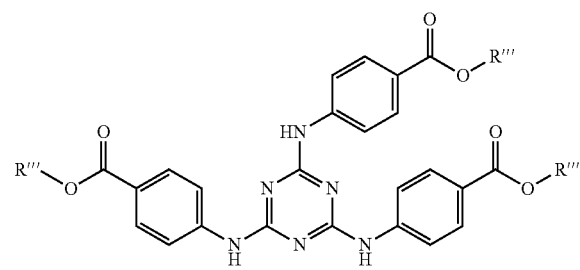

in which R''' denotes a 2-ethylhexyl radical
and mixtures thereof.

Among the triazine UVB-screening agents in accordance with the invention, mention may also be made of the silicone triazines of formula (VI) below, or a tautomeric form thereof:

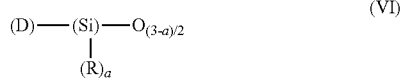

in which:

R, which may be identical or different, represent a linear or branched $C_1$-$C_{30}$ alkyl radical which is optionally halogenated or unsaturated, a $C_6$-$C_{12}$ aryl radical, a $C_1$-$C_{10}$ alkoxy radical, a hydroxyl radical or the trimethylsilyloxy group;

the group (D) denotes an s-triazine compound of formula (VII) below:

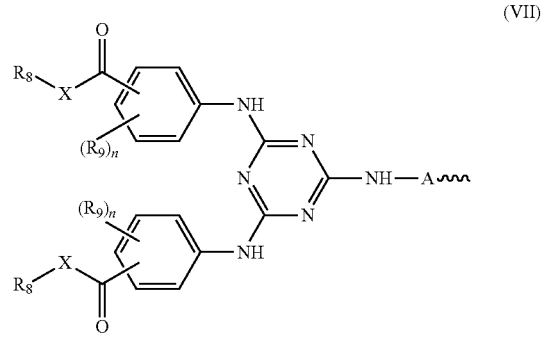

in which:

X represents —O— or —$NR_{10}$—, with $R_{10}$ representing hydrogen or a $C_1$-$C_5$ alkyl radical, $R_8$ represents a linear or branched $C_1$-$C_{30}$ alkyl radical which is optionally unsaturated and which may comprise a silicon atom, a $C_5$-$C_{20}$ cycloalkyl group, optionally substituted with 1 to 3 linear or branched $C_1$-$C_4$ alkyl radicals, the group —($CH_2CHR_{10}$—O$)_m R_{11}$ or the group —$CH_2$—CH(OH)—$CH_2$—O—$R_{12}$, $R_9$, which may be identical or different, represent a hydroxyl radical, a linear or branched $C_1$-$C_8$ alkyl radical or a $C_1$-$C_8$ alkoxy radical, it being possible for two adjacent $R_2$ groups on the same aromatic nucleus together to form an alkylidenedioxy group in which the alkylidene group contains 1 or 2 carbon atoms, $R_{10}$ represents hydrogen or methyl; it being possible for the group (C=O)$XR_8$ to be in the ortho, meta or para position relative to the amino group, $R_{11}$ represents hydrogen or a $C_1$-$C_8$ alkyl group, $R_{12}$ represent hydrogen or a $C_4$-$C_8$ alkyl group, m is an integer ranging from 2 to 20, n=0 to 2, A is a divalent radical chosen from methylene or a group corresponding to one of the following formulae (VIII), (IX), (X) or (XI):

in which:

Z is a saturated or unsaturated, linear or branched $C_1$-$C_{10}$ alkylene diradical, optionally substituted with a hydroxyl radical or oxygen atoms and optionally containing an amino group;

W represents a hydrogen atom, a hydroxyl radical or a linear or branched, saturated or unsaturated $C_1$-$C_8$ alkyl radical.

The organosiloxane of formula (VI) may comprise units of formula: $(R)_b—(Si)(O)_{(4-b)/2}$ in which R has the same meaning as in formula (VI), b=1, 2 or 3.

It should be noted that the derivatives of formula (VI) can be used in their tautomeric forms and more particularly in the tautomeric form of formula (VI') below:

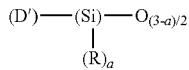
(VI')

in which the group (D') denotes an s-triazine compound of formula (VII') below:

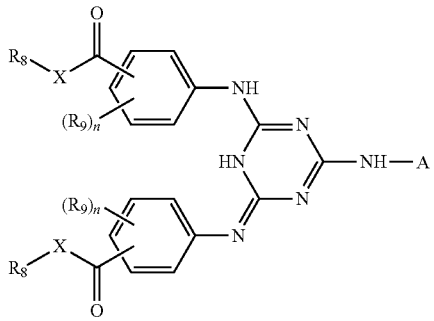
(VII')

In addition to the units of formula $-A-(Si)(R)_a(O)_{(3-a)/2}$, the organosiloxane may comprise units of formula $(R^1)_b—(Si)(O)_{(4-b)/2}$ in which $R^1$ has the same meaning as in formula (VI), b=1, 2 or 3.

In formulae (VI) and (VI') as defined above, the alkyl radicals may be linear or branched, saturated or unsaturated and chosen especially from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radical that is particularly preferred is the methyl radical.

The preferred s-triazine derivatives are those for which, in the formula (VI) or (VI'), at least one and even more preferentially all of the following characteristics are satisfied:
R is methyl,
a=1 or 2,
$R_8$ is a $C_2$-$C_8$ radical,
Z=—$CH_2$—,
W=H.

Preferably, the s-triazine compounds of formula (VI) of the invention are represented by formulae (VIa), (VIb) and (VIc) below:

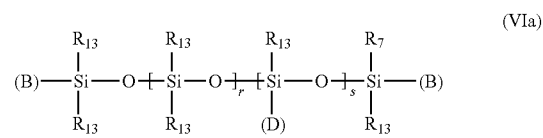
(VIa)

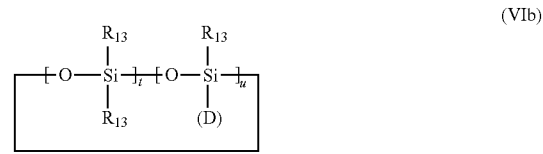
(VIb)

(VIc)

in which:
(D) corresponds to formula (VII) as defined above,
$R_{13}$, which may be identical or different, are chosen from linear or branched $C_1$-$C_{20}$ alkyl, phenyl, 3,3,3-trifluoropropyl and trimethylsilyloxy radicals or the hydroxyl radical,
$R_{14}$, which may be identical or different, are chosen from linear or branched $C_1$-$C_{20}$ alkyl and alkenyl radicals, hydroxyl radicals or phenyl radicals,
(B), which may be identical or different, are chosen from the $R_{13}$ radicals and the (D) radical,
r is an integer between 0 and 200 inclusive,
s is an integer ranging from 0 to 50 and, if s=0, at least one of the two (B) symbols denotes (D),
u is an integer ranging from 1 to 10,
t is an integer ranging from 0 to 10, it being understood that t+u is equal to or greater than 3, and the tautomeric forms thereof.

The linear diorganosiloxanes of formula (VIa)

The linear or cyclic diorganosiloxanes of formula (VIa) or (VIb) are random oligomers or polymers preferably having at least one and even more preferentially all of the following characteristics:

$R_{13}$ is a methyl radical, a $C_1$-$C_2$ alkoxy radical or a hydroxyl radical, B is preferentially methyl (in the case of the linear compounds of formula (VIa).

As examples of particularly preferred compounds of formula (VI), mention will be made of the compounds of formulae $(VI_1)$ to $(VI_{14})$ below and also the tautomeric forms thereof:

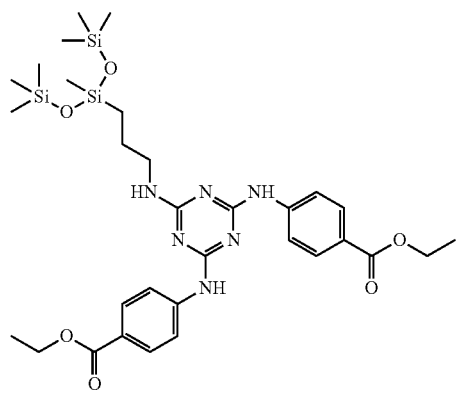
(VI₁)
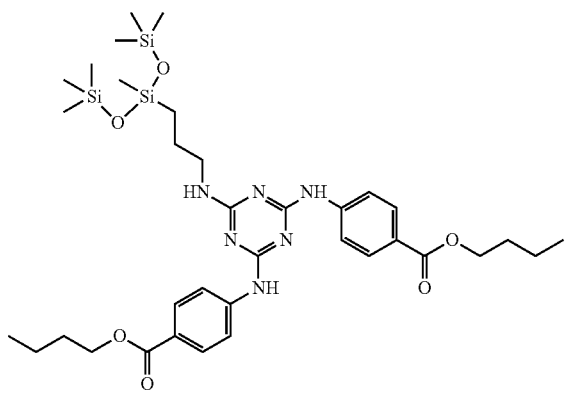
(VI₂)
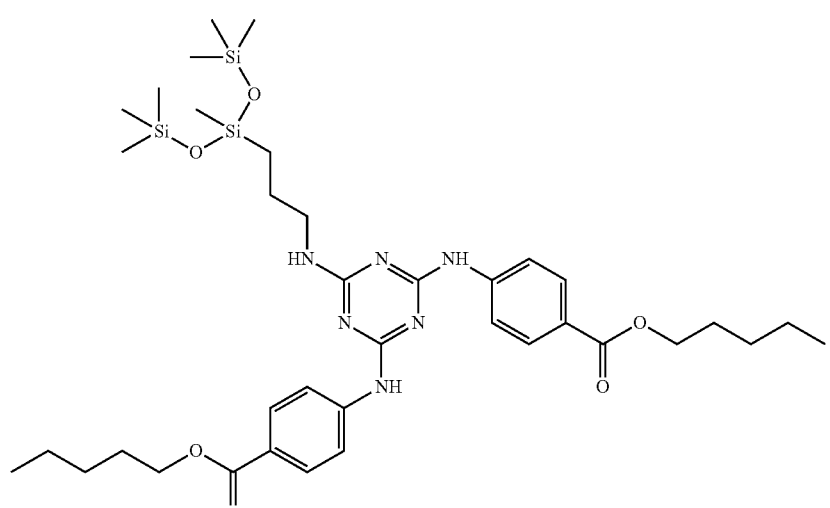
(VI₃)
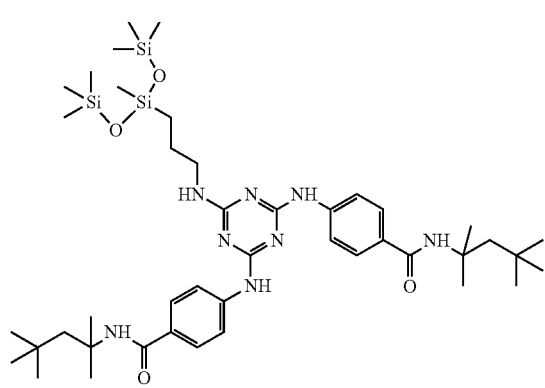
(VI₄)
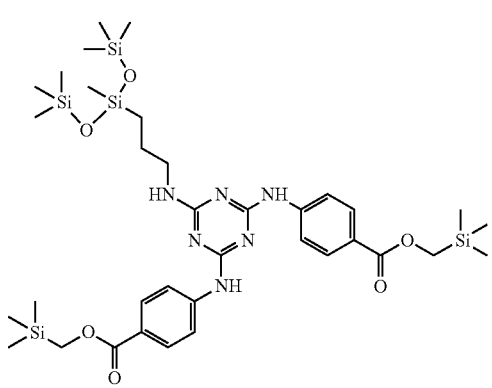
(VI₅)
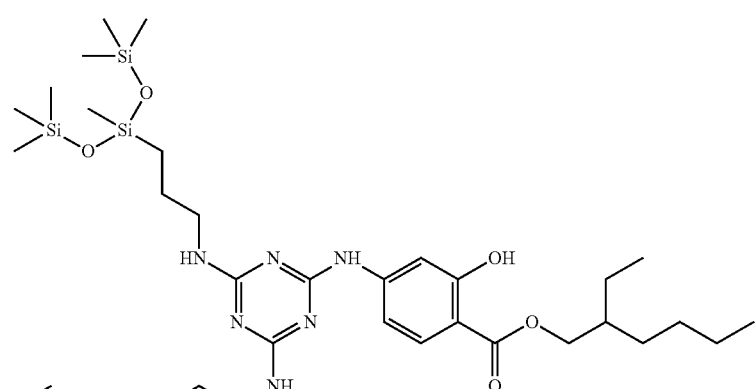
(VI₆)

Use will be made more particularly of the compound 2,4-bis(n-butyl 4'-diylaminobenzoate)-6-{[1,3,3,3-tetramethyl-1-[(trimethylsilyl)oxy]disiloxanyl]propyl-3-ylamino}-s-triazine of structure (VI₂):

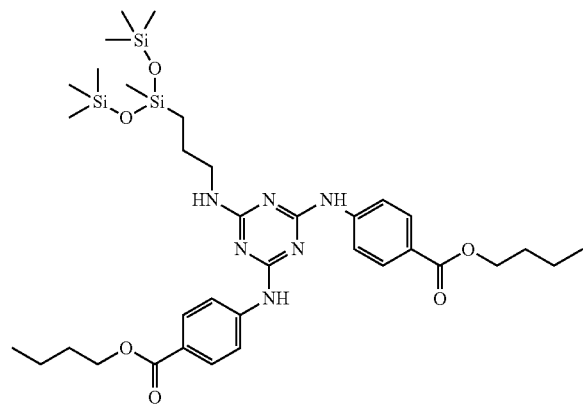

(VI₂)

The triazines of formula (VI) and the synthesis thereof were described in patent application EP 1 891 079.

Among the triazine UVB-screening agents that may be used according to the invention, mention may also be made of s-triazines substituted with a benzalmalonate and/or cinnamate and/or benzylidenecamphor and/or benzotriazole function, such as:

2,4,6-tris(diisobutyl 4'-aminobenzalmalonate)-s-triazine,
2,4,6-tris(bis(2-ethylhexyl) 4'-aminobenzalmalonate)-s-triazine,
2,4,6-tris(bis(2-ethylhexyl) 4'-aminobenzalmalonate)-6-chloro-s-triazine,
2,4,6-tris(bis(2-ethylhexyl) 4'-aminobenzalmalonate)-6-(2-ethylhexyl 4'-aminobenzoate)-s-triazine,
2,4,6-tris(diisobutyl 4'-aminobenzalmalonate)-6-butoxy-s-triazine,
2,4,6-tris(diisobutyl 4'-aminobenzalmalonate)-6-(2-ethylhexylamino)-s-triazine,
2,4-bis(4'-aminobenzylidenecamphor)-6-(2-ethylhexylamino)-s-triazine,
2,4-bis(4'-aminobenzylidenecamphor)-6-(diisobutyl 4'-aminobenzalmalonate)-s-triazine,
2,4,6-tris(diethyl 4'-aminobenzalmalonate)-s-triazine,
2,4,6-tris(diisopropyl 4'-aminobenzalmalonate)-s-triazine,
2,4,6-tris(dimethyl 4'-aminobenzalmalonate)-s-triazine,
2,4,6-tris(ethyl α-cyano-4-aminocinnamate)-s-triazine,
2,4,6-tris[(3'-benzotriazol-2-yl-2'-hydroxy-5'-methyl)phenylamino]-s-triazine,
2,4,6-tris[(3'-benzotriazol-2-yl-2'-hydroxy-5'-tert-octyl)phenylamino]-s-triazine.

The triazine UVB-screening agents according to the invention are preferably present in the compositions according to the invention in a concentration ranging from 0.1% to 30% by weight, preferentially from 0.2% to 20% by weight and even more preferentially from 0.5% to 10% by weight relative to the total weight of the composition.

Organic UVA-Screening Agents

The compositions according to the invention contain at least one organic UVA-screening agent. They are generally chosen from hydrophilic, lipophilic or insoluble organic UVA-screening agents.

The term "hydrophilic UV-screening agent" means any cosmetic or dermatological organic or mineral compound for screening out UV radiation, which can be fully dissolved in molecular form in a liquid aqueous phase or which can be dissolved in colloidal form (for example in micellar form) in a liquid aqueous phase.

The term "lipophilic screening agent" means any cosmetic or dermatological organic or mineral compound for screening out UV radiation, which can be fully dissolved in molecular form in a liquid fatty phase or which can be dissolved in colloidal form (for example in micellar form) in a liquid fatty phase.

The term "insoluble UV-screening agent" means any cosmetic or dermatological organic or mineral compound for screening out UV radiation which has a solubility in water of less than 0.5% by weight and a solubility of less than 0.5% by weight in the majority of organic solvents such as liquid paraffin, fatty alkyl benzoates and fatty acid triglycerides, for example Miglyol® 812 sold by the company Dynamit Nobel. This solubility, determined at 70° C., is defined as the amount of product in solution in the solvent at equilibrium with an excess of solid in suspension after returning to room temperature. It may be readily evaluated in the laboratory.

Among the organic UVA-screening agents of the invention, mention may be made of:
organic UVA-screening agents of the type (A) which are capable of exclusively absorbing UV rays between 320 and 400 nm,
organic UVA-screening agents of the type (B) which are capable of simultaneously absorbing UV rays between 280 and 320 nm and those between 320 and 400 nm, and mixtures thereof.

a) Organic UVA-Screening Agents of the Type (A) which are Capable of Absorbing UV Rays from 320 to 400 nm The organic UVA-screening agents of the type (A) are preferably chosen from dibenzoylmethane compounds; amino-substituted hydroxybenzophenone compounds as described in patent applications EP-A-1 046 391, EP 1 133 980, DE 100 12 408 and WO 2007/071 584; anthranilic compounds; benzylidenecamphor compounds; 4,4-diarylbutadiene compounds such as those described in patents EP 916 335 and EP 1 133 981; bis-benzazolyl compounds as described in patents EP 669 323 and U.S. Pat. No. 246,326; and mixtures thereof, and more particularly the following organic UVA-screening agents:

Dibenzoylmethane Compounds:
Butylmethoxydibenzoylmethane sold especially under the trade name Parsol 1789® by DSM Nutritional Products, Inc.;
Isopropyldibenzoylmethane.

Amino-Substituted Hydroxybenzophenone Compounds:
n-hexyl 2-(4-diethylamino-2-hydroxybenzoyl)benzoate sold under the trade name Uvinul A Plus® by the company BASF.
1,1'-(1,4-piperazinediyl)bis[1-[2-[4-(diethylamino)-2-hydroxybenzoyl]phenyl]methanone] (CAS 919803-06-8), such as described in patent application WO 2007/071 584; this compound advantageously being used in micronized form (mean size of 0.02 to 2 μm), which may be obtained, for example, according to the micronization process described in patent applications GB-A-2 303 549 and EP-A-893 119, and in particular in the form of an aqueous dispersion.

Anthranilic Compounds:
Menthyl anthranilate sold especially under the trade name Neo Heliopan MA® by Symrise.

4,4-Diarylbutadiene Compounds:
  1,1-dicarboxy(2,2'-dimethylpropyl)-4,4-diphenylbutadiene.
Benzylidenecamphor Compounds:
  Terephthalylidenedicamphorsulfonic acid manufactured under the name Mexoryl SX® by Chimex.
Bis-Benzazolyl Compounds:
  Disodium phenyldibenzimidazoletetrasulfonate sold under the trade name Neo Heliopan AP by Haarmann and Reimer.
  In the context of the invention, and according to a particular embodiment, the following organic screening agents of the type (A) are used:
    butylmethoxydibenzoylmethane;
    n-hexyl 2-(4-diethylamino-2-hydroxybenzoyl)benzoate;
    terephthalylidenedicamphorsulfonic acid, and mixtures thereof.
b) Organic UVA-Screening Agents of the Mixed Type (B) which are Capable of Absorbing Both UVA and UVB
  The organic UVA-screening agents of the type (B) are preferably chosen from benzophenone compounds; phenylbenzotriazole compounds; methylenebis(hydroxyphenylbenzotriazole) compounds as described in patent applications U.S. Pat. Nos. 5,237,071, 5,166,355, GB 2 303 549, DE 197 26 184 and EP 893 119; bis-resorcinyl triazine compounds as described in patent application EP 0 775 698; benzoxazole compounds as described in patent applications EP 0 832 642, EP 1 027 883, EP 1 300 137 and DE 101 62 844; symmetrical triazine screening agents substituted with naphthalenyl groups or polyphenyl groups described in patent U.S. Pat. No. 6,225,467, patent application WO 2004/085 412 (see compounds 6 and 9) or the document *Symmetrical Triazine Derivatives* IP.COM IPCOM000031257 Journal, INC West Henrietta, N.Y., US (20 Sep. 2004), especially 2,4,6-tris(diphenyl)triazine and 2,4,6-tris(terphenyl)triazine, which is reviewed in patent applications WO 06/035 000, WO 06/034 982, WO 06/034 991, WO 06/035 007, WO 2006/034 992 and WO 2006/034 985, these compounds being advantageously used in micronized form (mean particle size from 0.02 to 3 µm) which may be obtained, for example, according to the micronization process described in patent applications GB-A-2 303 549 and EP-A-893 119 and especially in aqueous dispersion form; and mixtures thereof.
Benzophenone Compounds
  Benzophenone-1 sold especially under the trade name Uvinul 400® by BASF;
  Benzophenone-2, sold especially under the trade name Uvinul D 50® by BASF;
  Benzophenone-3 or Oxybenzone, sold especially under the trade name Uvinul M 40® by BASF;
  Benzophenone-4 sold by the company BASF under the name Uvinul MS 40®;
  Benzophenone-5;
  Benzophenone-6 sold especially under the trade name Helisorb 11 by Norquay;
  Benzophenone-8 sold especially under the trade name Spectra-Sorb UV-24® by American Cyanamid;
  Benzophenone-9 sold by the company BASF under the name Uvinul DS 49®;
  Benzophenone-10;
  Benzophenone-11;
  Benzophenone-12.
Phenylbenzotriazole Compounds:
  Drometrizole trisiloxane sold especially under the name Silatrizole by Rhodia Chimie or manufactured under the name Meroxyl XL® by the company Chimex.
Methylenebis(hydroxyphenylbenzotriazole) Compounds
  Methylenebis(benzotriazolyl)tetramethylbutylphenol, sold in solid form especially under the trade name Mixxim BB/100® by Fairmount Chemical, or in the form of an aqueous dispersion of micronized particles with a mean particle size ranging from 0.01 to 5 µm, more preferentially from 0.01 to 2 µm and more particularly from 0.020 to 2 µm, with at least one alkylpolyglycoside surfactant having the structure $C_nH_{2n+1}O(C_8H_{10}O_5)_xH$, in which n is an integer from 8 to 16 and x is the mean degree of polymerization of the $(C_6H_{10}O_5)$ unit and ranges from 1.4 to 1.6, as described in patent GB-A-2 303 549, sold especially under the trade name Tinosorb M® by BASF, or in the form of an aqueous dispersion of micronized particles with a mean particle size ranging from 0.02 to 2 µm, more preferentially from 0.01 to 1.5 µm and more particularly from 0.02 to 1 µm, in the presence of at least one polyglyceryl mono($C_8$-$C_{20}$)alkyl ester with a degree of glycerol polymerization of at least 5, such as the aqueous dispersions described in patent application WO 2009/063 392.
Bis-Resorcinyl Triazine Compounds:
  Bis(ethylhexyloxyphenol)methoxyphenyltriazine sold especially under the trade name Tinosorb S® by BASF.
Benzoxazole Compounds:
  2,4-Bis[5-(1-dimethylpropyl)benzoxazol-2-yl-(4-phenyl)imino]-6-(2-ethylhexyl)imino-1,3,5-triazine, sold especially under the name Uvasorb K2A by Sigma 3V.
  In the context of the invention, and according to a particular embodiment, the following organic screening agents (B) are used:
    Drometrizole Trisiloxane,
    Methylenebis(benzotriazolyl)tetramethylbutylphenol in the form of an aqueous dispersion of micronized particles,
    Bis(ethylhexyloxyphenol)methoxyphenyltriazine,
    Benzophenone-3 or Oxybenzone,
    2,4,6-tris(diphenyl)triazine in micronized form,
    and mixtures thereof.
  The organic UVA-screening agents in accordance with the invention are preferably present in contents ranging from 0.01% to 30% by weight and preferably from 0.1% to 15% by weight relative to the total weight of the composition.
Oily Phase
  The compositions in accordance with the invention comprise at least one oily phase.
  The compositions of the invention contain less than 2% of cyclohexasiloxane relative to the total weight of the composition since this compound may pose incompatibility problems with certain oils usually used in antisun formulations.
  For the purposes of the invention, the term "oily phase" means a phase comprising at least one oil and all of the liposoluble and lipophilic ingredients and the fatty substances used for the formulation of the compositions of the invention.
  The term "oil" means any fatty substance which is in liquid form at room temperature (20-25° C.) and at atmospheric pressure (760 mmHg).
  An oil that is suitable for use in the invention may be volatile or non-volatile.
  An oil that is suitable for use in the invention may be chosen from hydrocarbon-based oils, silicone oils and fluoro oils, and mixtures thereof.
  A hydrocarbon-based oil that is suitable for use in the invention may be an animal hydrocarbon-based oil, a plant hydrocarbon-based oil, a mineral hydrocarbon-based oil or a synthetic hydrocarbon-based oil.

An oil that is suitable for use in the invention may be advantageously chosen from mineral hydrocarbon-based oils, plant hydrocarbon-based oils, synthetic hydrocarbon-based oils and silicone oils, and mixtures thereof.

For the purposes of the present invention, the term "silicone oil" means an oil comprising at least one silicon atom, and especially at least one Si—O group.

The term "hydrocarbon-based oil" means an oil comprising mainly hydrogen and carbon atoms.

The term "fluoro oil" means an oil comprising at least one fluorine atom.

A hydrocarbon-based oil that is suitable for use in the invention may also optionally comprise oxygen, nitrogen, sulfur and/or phosphorus atoms, for example in the form of hydroxyl, amine, amide, ester, ether or acid groups, and in particular in the form of hydroxyl, ester, ether or acid groups.

The oily phase generally comprises, in addition to the lipophilic UV-screening agent(s), at least one volatile or non-volatile hydrocarbon-based oil and/or one volatile and/or non-volatile silicone oil.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil which remains on the skin or the keratin fibre, at room temperature and atmospheric pressure, for at least several hours and which in particular has a vapour pressure of less than $10^{-3}$ mmHg (0.13 Pa).

Hydrocarbon-Based Oils

As non-volatile hydrocarbon-based oils that may be used according to the invention, mention may be made especially of:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheatgerm oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passionflower oil and musk rose oil; or also caprylic/capric acid triglycerides, such as those sold by Stéarineries Dubois or those sold under the names Miglyol 810®, 812® and 818® by Dynamit Nobel, (ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane, and mixtures thereof;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms, on condition that R+R' is ≥10, for instance purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226® by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of Dub Dis by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates such as dicaprylyl carbonate, for instance the product sold under the name Cetiol CC® by the company Cognis;

(viii) fatty amides, such as isopropyl N-lauroyl sarcosinate, such as the product sold under the trade name Eldew SL205® from Ajinomoto;

and mixtures thereof.

Among the non-volatile hydrocarbon-based oils that may be used according to the invention, preference will be given more particularly to glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, in particular octyldodecanol.

As volatile hydrocarbon-based oils that may be used according to the invention, mention may be made especially of hydrocarbon-based oils having from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched $C_8$-$C_{16}$ esters, isohexyl neopentanoate, and mixtures thereof.

Mention may also be made of the alkanes described in the Cognis patent applications WO 2007/068 371 or WO 2008/155 059 (mixtures of distinct alkanes differing by at least one carbon). These alkanes are obtained from fatty alcohols, which are themselves obtained from coconut or palm oil. Mention may be made of the mixtures of n-undecane ($C_{11}$) and n-tridecane ($C_{13}$) obtained in Examples 1 and 2 of patent application WO 2008/155 059 from the company Cognis. Mention may also be made of n-dodecane ($C_{12}$) and n-tetradecane ($C_{14}$) sold by Sasol under the respective references Parafol 12-97 and Parafol 14-97®, and also mixtures thereof.

Other volatile hydrocarbon-based oils, for instance petroleum distillates, especially those sold under the name Shell Solt® by the company Shell, may also be used. According to one embodiment, the volatile solvent is chosen from volatile hydrocarbon-based oils containing from 8 to 16 carbon atoms, and mixtures thereof.

Silicone Oils

The non-volatile silicone oils may be chosen in particular from non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Examples of volatile silicone oils that may be mentioned include volatile linear or cyclic silicones, especially those with a viscosity ≤8 centistokes ($8 \times 10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general formula (I):

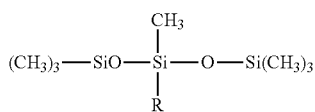

where R represents an alkyl group comprising from 2 to 4 carbon atoms, one or more hydrogen atoms of which may be replaced with a fluorine or chlorine atom.

Among the oils of general formula (I), mention may be made of:
 3-butyl-1,1,1,3,5,5,5-heptamethyltrisiloxane,
 3-propyl-1,1,1,3,5,5,5-heptamethyltrisiloxane, and
 3-ethyl-1,1,1,3,5,5,5-heptamethyltrisiloxane,
corresponding to the oils of formula (I) for which R is, respectively, a butyl group, a propyl group or an ethyl group.

Fluoro Oils

Use may also be made of volatile fluoro oils, such as nonafluoromethoxybutane, decafluoropentane, tetradecafluorohexane, dodecafluoropentane, and mixtures thereof.

An oily phase according to the invention may also comprise other fatty substances, mixed with or dissolved in the oil.

Another fatty substance that may be present in the oily phase may be, for example:
 a fatty acid chosen from fatty acids comprising from 8 to 30 carbon atoms, such as stearic acid, lauric acid, palmitic acid and oleic acid;
 a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;
 a gum chosen from silicone gums (dimethiconol);
 a pasty compound, such as polymeric or non-polymeric silicone compounds, esters of a glycerol oligomer, arachidyl propionate, fatty acid triglycerides and derivatives thereof;
and mixtures thereof.

According to a particular form of the invention, the overall oily phase, including all the lipophilic substances of the composition that are capable of being dissolved in this same phase, represents from 5% to 95% by weight and preferably from 10% to 80% by weight, relative to the total weight of the composition.

Aqueous Phase

The compositions according to the invention may also comprise at least one aqueous phase, especially in the case where it is desired to use a hydrophilic organic UVA-screening agent.

The aqueous phase comprises water and optionally other water-soluble or water-miscible organic solvents.

An aqueous phase that is suitable for use in the invention may comprise, for example, a water chosen from a natural spring water, such as water from La Roche-Posay, water from Vittel or waters from Vichy, or a floral water.

The water-soluble or water-miscible solvents that are suitable for use in the invention comprise short-chain monoalcohols, for example $C_1$-$C_4$ monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may more particularly be made of ethanol, propylene glycol, glycerol, and mixtures thereof.

According to a specific form of the invention, the overall aqueous phase, including all the hydrophilic substances of the composition capable of being dissolved in this same phase, represents from 5% to 95% by weight and preferably from 10% to 80% by weight, with respect to the total weight of the composition.

Additives a) Additional UV-Screening Agents

The compositions according to the invention may also contain one or more additional UV-screening agents chosen from hydrophilic, lipophilic, non-liquid or insoluble organic UVB-screening agents and/or one or more mineral UV-screening agents. It will preferentially consist of at least one hydrophilic, lipophilic or insoluble organic UV-screening agent.

The term "organic UVB-screening agent" means any organic chemical molecule that is capable exclusively of absorbing UVB rays in the wavelength range between 280 and 320 nm.

The additional organic UV-screening agents are especially chosen from p-aminobenzoic (PABA) compounds; triazine compounds; benzylidenecamphor compounds; imidazoline compounds; benzalmalonate compounds, especially those mentioned in patent U.S. Pat. No. 5,624,663; benzimidazole compounds; benzoxazole compounds; screening silicones and polymers, and mixtures thereof.

As examples of additional organic UV-screening agents, mention may be made of those denoted hereinbelow under their INCI name:

Para-Aminobenzoic Compounds:
 PABA,
 Ethyl PABA,
 Ethyl Dihydroxypropyl PABA,
 Ethylhexyl Dimethyl PABA, sold especially under the name Escalol 507® by ISP, Glyceryl PABA,
 PEG-25 PABA, sold under the name Uvinul P 25® by BASF.

Benzylidenecamphor Compounds:

3-Benzylidenecamphor, manufactured under the name Mexoryl SD® by Chimex, 4-Methylbenzylidenecamphor, sold under the name Eusolex 6300® by Merck, Polyacrylamidomethylbenzylidenecamphor, manufactured under the name Mexoryl SW® by Chimex.

Imidazoline Compounds:

Ethylhexyl dimethoxybenzylidene dioxoimidazoline Propionate.

Benzalmalonate Compounds:

Polyorganosiloxanes containing benzalmalonate functions, for instance Polysilicone-15, sold especially under the trade name Parsol SLX by DSM Nutritional Products, Inc.; Dineopentyl 4'-methoxybenzalmalonate.

The mineral UV-screening agents used in accordance with the present invention are metal oxide pigments. More preferentially, the mineral UV-screening agents of the invention are metal oxide particles with a mean elementary particle size of less than or equal to 0.5 µm, more preferentially between 0.005 and 0.5 µm, even more preferentially between 0.01 and 0.2 µm, better still between 0.01 and 0.1 µm and more particularly between 0.015 and 0.05 µm.

They may be selected in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:

with silica, such as the product Sunveil® from the company Ikeda, with silica and iron oxide, such as the product Sunveil F® from the company Ikeda, with silica and alumina, such as the products Microtitanium Dioxide MT 500 SAO and Microtitanium Dioxide MT 100 SAO from the company Tayca, and Tioveil from the company Tioxide, with alumina, such as the products Tipaque TTO-55 (B)® and Tipaque TTO-55 (A)® from the company Ishihara and UVT 14/4 from the company Sachtleben Pigments, with alumina and aluminium stearate, such as the products Microtitanium Dioxide MT 100 T®, MT 100 TX®, MT 100 Z® and MT-01® from the company Tayca, the products Solaveil CT-10 W® and Solaveil CT 100® from the company Uniqema and the product Eusolex T-AVO® from the company Merck, with silica, alumina and alginic acid, such as the product MT-100 AQ® from the company Tayca, with alumina and aluminium laurate, such as the product Microtitanium Dioxide MT 100 S® from the company Tayca, with iron oxide and iron stearate, such as the product Microtitanium Dioxide MT 100 F® from the company Tayca, with zinc oxide and zinc stearate, such as the product BR 351® from the company Tayca, with silica and alumina and treated with a silicone, such as the products Microtitanium Dioxide MT 600 SAS®, Microtitanium Dioxide MT 500 SAS® or Microtitanium Dioxide MT 100 SAS® from the company Tayca, with silica, alumina and aluminium stearate and treated with a silicone, such as the product STT-30-DS® from the company Titan Kogyo, with silica and treated with a silicone, such as the product UV-Titan X 195® from the company Sachtleben Pigments, with alumina and treated with a silicone, such as the products Tipaque TTO-55 (S)® from the company Ishihara or UV Titan M 262® from the company Sachtleben Pigments, with triethanolamine, such as the product STT-65-S from the company Titan Kogyo, with stearic acid, such as the product Tipaque TTO-55 (C)® from the company Ishihara, with sodium hexametaphosphate, such as the product Microtitanium Dioxide MT 150 W® from the company Tayca.

$TiO_2$ treated with octyltrimethylsilane, sold under the trade name T 805® by the company Degussa Silices, $TiO_2$ treated with a polydimethylsiloxane, sold under the trade name 70250 Cardre UF TiO2SI3® by the company Cardre, anatase/rutile $TiO_2$ treated with a polydimethylhydrosiloxane, sold under the trade name Microtitanium Dioxide USP Grade Hydrophobic® by the company Color Techniques.

Mention may also be made of $TiO_2$ pigments doped with at least one transition metal such as iron, zinc or manganese and more particularly manganese. Preferably, the said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of $TiO_2$ particles doped with manganese in capric/caprylic acid triglyceride in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wackher under the name Transparent Titanium Oxide PW®, by the company Miyoshi Kasei under the name UFTRO, by the company Tomen under the name ITS® and by the company Tioxide under the name Tioveil AQ®.

The uncoated zinc oxide pigments are for example:

those sold under the name Z-Cote by the company Sunsmart;

those sold under the name Nanox® by the company Elementis;

those sold under the name Nanogard WCD 2025® by the company Nanophase Technologies.

The coated zinc oxide pigments are for example:

those sold under the name Zinc Oxide CS-5® by the company Toshibi (ZnO coated with polymethylhydrogenosiloxane);

those sold under the name Nanogard Zinc Oxide FN® by the company Nanophase Technologies (as a 40% dispersion in Finsolv TN®, $C_{12}$-$C_{15}$ alkyl benzoate);

those sold under the name Daitopersion Zn-30® and Daitopersion Zn-50® by the company Daito (dispersions in cyclopolymethylsiloxane/oxyethylenated polydimethylsiloxane, containing 30% or 50% of zinc oxides coated with silica and polymethylhydrogenosiloxane);

those sold under the name NFD Ultrafine ZnO® by the company Daikin (ZnO coated with perfluoroalkyl phosphate and copolymer based on perfluoroalkylethyl as a dispersion in cyclopentasiloxane);

those sold under the name SPD-Z1® by the company Shin-Etsu (ZnO coated with silicone-grafted acrylic polymer, dispersed in cyclodimethylsiloxane);

those sold under the name Escalol Z100® by the company ISP (alumina-treated ZnO dispersed in an ethylhexyl methoxycinnamate/PVP-hexadecene copolymer/methicone mixture);

those sold under the name Fuji ZnO-SMS-10® by the company Fuji Pigment (ZnO coated with silica and polymethylsilsesquioxane);

those sold under the name Nanox Gel TN® by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company Rhône-Poulenc.

The uncoated iron oxide pigments are sold, for example, by the company Arnaud under the names Nanogard WCD 2002® (FE 45B®), Nanogard Iron FE 45 BL AQ®, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

The additional UV-screening agents according to the invention are preferably present in the compositions according to the invention in a content ranging from 0.1% to 45% by weight and in particular from 1% to 30% by weight relative to the total weight of the composition.

b) Other Additives:

The compositions in accordance with the present invention may also comprise conventional cosmetic adjuvants chosen in particular from organic solvents, ionic or nonionic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, basifying or acidifying agents or any other ingredient commonly used in the cosmetic and/or dermatological field.

Mention may be made, among organic solvents, of alcohols other than $C_1$-$C_4$ monoalcohols as defined above and in particular short-chain $C_2$-$C_8$ polyols, such as glycerol or diols, such as caprylyl glycol, 1,2-pentanediol, propanediol, butanediol, glycols and glycol ethers, such as ethylene glycol, propylene glycol, butylene glycol, dipropylene glycol or diethylene glycol.

Mention may be made, as thickeners, of carboxyvinyl polymers, such as the Carbopols® (Carbomers) and the Pemulens, such as Pemulen TR1® and Pemulen TR2® (acrylate/$C_{10}$-$C_{30}$ alkyl acrylate copolymer); polyacrylamides, for instance the crosslinked copolymers sold under the names Sepigel 305® (CTFA name: polyacrylamide/$C_{13-14}$ isoparaffin/Laureth 7) or Simulgel 600 (CTFA name: acrylamide/sodium acryloyldimethyl taurate copolymer/isohexadecane/polysorbate 80) by the company SEPPIC; 2-acrylamido-2-methylpropanesulfonic acid polymers and copolymers, optionally crosslinked and/or neutralized, such as the poly(2-acrylamido-2-methylpropanesulfonic acid) sold by the company Hoechst under the trade name Hostacerin AMPS® (CTFA name: ammonium polyacryloyldimethyl taurate) or Simulgel 800®, sold by the company SEPPIC (CTFA name: sodium polyacryloyldimethyl taurate/polysorbate 80/sorbitan oleate); copolymers of 2-acrylamido-2-methylpropanesulfonic acid and of hydroxyethyl acrylate, such as Simulgel NS® and Sepinov EMT 10@, sold by the company SEPPIC; cellulose derivatives, such as hydroxyethylcellulose; polysaccharides and in particular gums, such as xanthan gum; water-soluble or water-dispersible silicone derivatives, such as acrylic silicones, polyether silicones and cationic silicones, and mixtures thereof.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide or potassium hydroxide.

Preferably, the cosmetic composition comprises one or more basifying agents selected from alkanolamines, in particular triethanolamine, and sodium hydroxide.

In the case of a direct emulsion, the pH of the composition in accordance with the invention is generally between 3 and 12 approximately, preferably between 5 and 11 approximately and more particularly still from 6 to 8.5.

Among the active agents for caring for keratin materials such as the skin, the lips, the scalp, the hair, the eyelashes or the nails, examples that may be mentioned include:

vitamins and derivatives or precursors thereof, alone or as mixtures;
antioxidants;
free-radical scavengers;
antipollution agents;
self-tanning agents;

antiglycation agents;
calmatives;
deodorants;
essential oils;
NO-synthase inhibitors;
agents for stimulating the synthesis of dermal or epidermal macromolecules and/or for preventing the degradation thereof;
agents for stimulating fibroblast proliferation;
agents for stimulating keratinocyte proliferation;
muscle relaxants;
refreshing agents;
tensioning agents;
mattifying agents;
depigmenting agents;
propigmenting agents;
keratolytic agents;
desquamating agents;
moisturizers;
antiinflammatory agents;
antimicrobial agents;
slimming agents;
agents acting on the energy metabolism of cells;
insect repellents;
substance P or CGRP antagonists;
hair-loss counteractants;
antiwrinkle agents;
antiageing agents.

A person skilled in the art will select the said active principle(s) according to the effect desired on the skin, the hair, the eyelashes, the eyebrows or the nails.

Needless to say, a person skilled in the art will take care to select the abovementioned optional additional compound(s) and/or the amounts thereof such that the advantageous properties intrinsically associated with the compositions in accordance with the invention are not, or are not substantially, adversely affected by the envisaged addition(s).

Galenical Forms

The compositions according to the invention may be prepared according to the techniques that are well known to those skilled in the art. They may in particular be in the form of a simple or complex emulsion (O/W, W/O, O/W/O or W/O/W), such as a cream, a milk or a cream gel.

They may also be in anhydrous form, for instance in the form of an oil. The term "anhydrous composition" means a composition containing less than 1% by weight of water, or even less than 0.5% water, and especially free of water, the water not being added during the preparation of the composition but corresponding to the residual water provided by the mixed ingredients. They may optionally be packaged in aerosol form and may be in the form of a mousse or a spray.

In the case of compositions in the form of oil-in-water or water-in-oil emulsions, the emulsification processes that may be used are of the paddle or impeller, rotor-stator and HPH type.

In order to obtain stable emulsions with a low content of polymer (oil/polymer ratio >25), it is possible to prepare the dispersion in concentrated phase and then to dilute the dispersion with the remainder of the aqueous phase.

It is also possible, by means of an HPH (between 50 and 800 bar), to obtain stable dispersions with droplet sizes that may be as low as 100 nm.

The emulsions generally comprise at least one emulsifier chosen from amphoteric, anionic, cationic and nonionic emulsifiers, used alone or as a mixture. The emulsifiers are appropriately chosen according to the emulsion to be obtained (W/O or O/W).

Examples of W/O emulsifying surfactants that may be mentioned include alkyl esters or ethers of sorbitan, of glycerol, of polyol or of sugars; silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE 09® by the company Goldschmidt. One or more coemulsifiers may also be added thereto, which may be chosen advantageously from the group consisting of polyol alkyl esters.

Mention may also be made of non-silicone emulsifying surfactants, in particular alkyl esters or ethers of sorbitan, of glycerol, of polyol or of sugars.

Polyol alkyl esters that may especially be mentioned include polyethylene glycol esters, for instance PEG-30 dipolyhydroxystearate, such as the product sold under the name Arlacel P135® by the company ICI.

Examples of glycerol and/or sorbitan esters that may be mentioned include polyglyceryl isostearate, such as the product sold under the name Isolan GI 34® by the company Goldschmidt; sorbitan isostearate, such as the product sold under the name Arlacel 987® by the company ICI; sorbitan glyceryl isostearate, such as the product sold under the name Arlacel 986® by the company ICI, and mixtures thereof.

For the O/W emulsions, examples of nonionic emulsifying surfactants that may be mentioned include polyoxyalkylenated (more particularly polyoxyethylenated and/or polyoxypropylenated) esters of fatty acids and of glycerol; oxyalkylenated esters of fatty acids and of sorbitan; polyoxyalkylenated (in particular polyoxyethylenated and/or polyoxypropylenated) esters of fatty acids, optionally in combination with an ester of fatty acid and of glycerol, such as the PEG-100 Stearate/Glyceryl Stearate mixture sold, for example, by ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000® and Plantaren 1200®, cetearyl glucoside, optionally as a mixture with cetearyl alcohol, sold, for example, under the name Montanov 68® by the company SEPPIC, under the name Tegocare CG90® by the company Goldschmidt and under the name Emulgade KE3302® by the company Henkel, and arachidyl glucoside, for example in the form of the mixture of arachidyl and behenyl alcohols and of arachidyl glucoside sold under the name Montanov 202® by the company SEPPIC. According to a particular embodiment of the invention, the mixture of the alkyl polyglucoside as defined above with the corresponding fatty alcohol may be in the form of a self-emulsifying composition, for example as described in document WO-A-92/06778.

When it is an emulsion, the aqueous phase of this emulsion may comprise a nonionic vesicular dispersion prepared according to known processes (Bangham, Standish and Watkins, J. Mol. Biol., 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention consists of the use of the compositions according to the invention as defined above for the manufacture of cosmetic products for treating the skin, the lips, the nails, the hair, the eyelashes, the eyebrows and/or the scalp, especially care products, antisun products and makeup products.

The cosmetic compositions according to the invention may be used, for example, as makeup products.

Another subject of the present invention consists of a non-therapeutic cosmetic process for caring for and/or making up a keratin material, which consists in applying, to the surface of the said keratin material, at least one composition according to the invention as defined above.

The cosmetic compositions according to the invention may be used, for example, as care products and/or antisun products for the face and/or body with a liquid to semi-liquid consistency, such as milks, more or less smooth creams, cream gels or pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

Assembly

According to another aspect, the invention also relates to a cosmetic assembly comprising:

i) a container delimiting one or more compartment(s), the said container being closed by a closing member and optionally being unsealed; and ii) a makeup and/or care composition in accordance with the invention placed inside the said compartment(s).

The container may be, for example, in the form of a jar or a box.

The closing member may be in the form of a lid comprising a cap mounted so as to be able to move by translation or by pivoting relative to the container housing the said makeup and/or care composition(s).

The examples that follow serve to illustrate the invention without, however, being limiting in nature. In these examples, the amounts of the composition ingredients are given as weight percentages relative to the total weight of the composition.

EXAMPLES

A. Examples of Preparation of Merocyanine UV-Absorbing Agents

Example A1

Preparation of Compound (1)

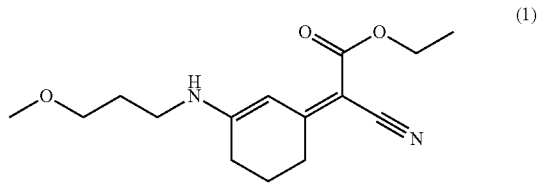 [SMILES: CCOC(=O)/C(C#N)=C1\C=C(NCCCOC)CCC1]

122.23 g of 3-[(3-methoxypropyl)amino]-2-cyclohexen-1-one were alkylated with dimethyl sulfate or alternatively with diethyl sulfate and treated with 75.45 g of ethyl cyanoacetate in approximately equimolar proportions in the presence of a base and optionally of a solvent.

The following base/solvent combinations were used:

| Example | Base | Solvent |
|---|---|---|
| Example A1.1 | DBU (1,8-diazabicyclo[5.4.0]undec-7-ene) | dimethylacetamide |
| Example A1.2 | triethylamine | isopropanol |
| Example A1.3 | 3-methoxypropylamine | isopropanol |
| Example A1.4 | 3-methoxypropylamine | tert-amyl alcohol |
| Example A1.5 | 3-methoxypropylamine | toluene |
| Example A1.6 | 3-methoxypropylamine | dimethylformamide |
| Example A1.7 | 3-methoxypropylamine | no solvent |
| Example A1.8 | N-morpholine | isopropanol |

The completion of the alkylation reaction was monitored, for example, via methods such as TLC, GC or HPLC.

162.30 g of compound (14) are obtained in the form of a brown oil.

After crystallization, the product was obtained in the form of yellowish crystals. Melting point: 92.7° C.

Example A2

Preparation of Compound (2)

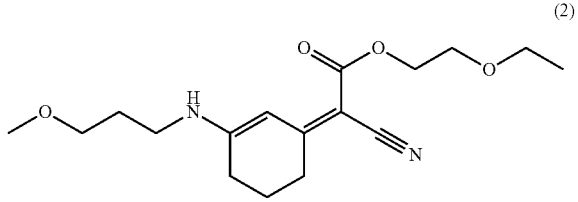 [SMILES: CCOCCOC(=O)/C(C#N)=C1\C=C(NCCCOC)CCC1]

148.4 g of 3-[(3-methoxypropyl)amino]-2-cyclohexen-1-one were alkylated with dimethyl sulfate or alternatively with diethyl sulfate and treated with 130.00 g of 2-ethoxyethyl cyanoacetate in the presence of an organic base and a solvent.

The following base/solvent combinations were used:

| Example | Base | Solvent |
|---|---|---|
| Example A2.1 | DBU (1,8-diazabicyclo[5.4.0]undec-7-ene) | dimethylacetamide |
| Example A2.2 | triethylamine | isopropanol |
| Example A2.3 | 3-methoxypropylamine | isopropanol |
| Example A2.4 | N-methylmorpholine | tert-amyl alcohol |
| Example A2.5 | 3-methoxypropylamine | toluene |
| Example A2.6 | 3-methoxypropylamine | dimethylformamide |
| Example A2.7 | 3-methoxypropylamine | No solvent |

Example A3 (Outside the Invention)

Preparation of the Compound (2Z)-2-cyano-N-(3-methoxypropyl)-2-{3-[(3-methoxypropyl)amino]cyclohex-2-en-1-ylidene}ethanamide described in the unpublished patent application PCT/EP 2012/064 195

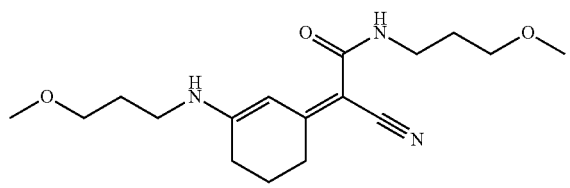

101.00 g of 3-[(3-methoxypropyl)amino]-2-cyclohexen-1-one were alkylated with dimethyl sulfate or alternatively with diethyl sulfate and treated with 86.00 g of 2-cyano-N-(3-methoxypropyl)acetamide in approximately equimolar proportions in the presence of a base and optionally of a solvent.

The following base/solvent combinations were used:

| Example | Base | Solvent |
|---|---|---|
| Example A3.1 | DBU (1,8-diazabicyclo[5.4.0]undec-7-ene) | dimethylacetamide |
| Example A3.2 | triethylamine | isopropanol |
| Example A3.3 | 3-methoxypropylamine | isopropanol |
| Example A3.4 | 3-methoxypropylamine | tert-amyl alcohol |
| Example A3.5 | 3-methoxypropylamine | toluene |
| Example A3.6 | 3-methoxypropylamine | dimethylformamide |
| Example A3.7 | 3-methoxypropylamine | no solvent |

The crude product (2Z)-2-cyano-N-(3-methoxypropyl)-2-{3-[(3-methoxypropyl)amino]cyclohex-2-en-1-ylidene}ethanamide was obtained in the form of a dark brown oil. After chromatography on a column of silica gel (eluent: 99/1 toluene/methanol), 81.8 g of product are obtained in the form of yellowish crystals.

Melting point: 84.7-85.3° C.

B.1 Formulation Examples 1 to 4

The compound 2-ethoxyethyl (2Z)-cyano{3-[(3-methoxypropyl)amino]cyclohex-2-en-1-ylidene} (2) of the invention was compared with:
- the compound (2Z)-2-cyano-N-(3-methoxypropyl)-2-{3-[(3-methoxypropyl)amino]cyclohex-2-en-1-ylidene}ethanamide according to Example A3 (outside the invention)
- the compound octyl-5-N,N-diethylamino-2-phenysulfonyl-2,4-pentadienoate (outside the invention),
- the merocyanine compound MC11 disclosed in the application WO2008/090066 (outside the invention).

Formulations 1 to 4 below were prepared; they were constructed such that the sum of the contents of oil and of liposoluble UV-screening agents remains constant. The content of the screening agents was adjusted so as to ensure the same level of UVB screening and also the same in vitro SPF, and also the same absorbance profile between 290 and 340 nm. For each of the formulations, the in vitro SPF, the in vitro $UVA_{PPD}$ index and the absorbance after 24 hours at room temperature and after 10 days at 60° C. were measured.

| Phase | INCI name | Formulation 1 (outside the invention) | Formulation 2 (outside the invention) | Formulation 3 (outside the invention) | Formulation 4 (invention) |
|---|---|---|---|---|---|
| A | Water | qsp 100 | qsp 100 | qsp 100 | qsp 100 |
|  | Glycerol | 6 | 6 | 6 | 6 |
|  | Disodium EDTA | 0.1 | 0.1 | 0.1 | 0.1 |
|  | Potassium Cetyl Phosphate (Amphisol K ®) | 1 | 1 | 1 | 1 |
|  | Triethanolamine | 0.45 | 0.45 | 0.45 | 0.45 |
| B | 2-Ethylphenyl benzoate (X-Tend 226 ®) | 19.4 | 18.5 | 18.2 | 18.1 |
|  | Octocrylene (UVINUL N539 ®) | 8 | 8.5 | 8.5 | 8.5 |
|  | Butylmethoxydibenzoylmethane (Parsol 1789 ®) | 2.6 | 2 | 2 | 2 |
|  | Octyl 5-N,N-diethylamino-2-phenylsulfonyl-2,4-pentadienoate | — | 1 | — | — |
|  | (2Z)-2-cyano-N-(3-methoxypropyl)-2-{3-[(3-methoxypropyl)amino]cyclohex-2-en-1-ylidene}ethanamide | — | — | 1.3 | — |
|  | Compound (2) | — | — | — | 1.4 |
|  | Stearic Acid | 1.5 | 1.5 | 1.5 | 1.5 |
|  | Glyceryl stearate (and) PEG-100 stearate (Arlacel 165) | 1.5 | 1.5 | 1.5 | 1.5 |
|  | Dimethicone | 0.5 | 0.5 | 0.5 | 0.5 |
|  | Preservatives | 1.28 | 1.28 | 1.28 | 1.28 |

| Phase | INCI name | Formulation 1 (outside the invention) | Formulation 2 (outside the invention) | Formulation 3 (outside the invention) | Formulation 4 (invention) |
|---|---|---|---|---|---|
| C | Isohexadecane | 2 | 2 | 2 | 2 |
|  | Xanthan gum | 0.1 | 0.1 | 0.1 | 0.1 |
|  | Acrylates/C10-30 alkyl acrylate crosspolymer (Pemulen TR1 ®) | 0.25 | 0.25 | 0.25 | 0.25 |
| D | Triethanolamine | 0.25 | 0.25 | 0.25 | 0.25 |
| E | Alcohol | 2 | 2 | 2 | 2 |
| in vitro SPF ($t_{24\,h}$) | | 15.1 ± 2.3 | 13.6 ± 1.8 | 11.2 ± 1.6 | 11.8 ± 3.1 |
| in vitro $UVA_{PPD}$ ($t_{24\,h}$) | | 10.4 ± 1.3 | 11.6 ± 1.5 | 10.3 ± 1.4 | 10.8 ± 2.7 |

The formulations 5 to 9 below were prepared. The content of the filters was constant in order to compare the performance of the compound (2) to the one of (2Z)-2-cyano-N-(3-methoxy-propyl)-2-{3-[(3-meth-oxypropyl)amino]cyclohex-2-en-1-ylidene}-ethanamide according to example A3 (outside the invention) and to the one of the compound MC11 disclosed in the application WO2008/090066 (outside the invention) at the same content. For the formulations 5 and 6, SPF, $UVA_{PPD}$ index and absorbance were measured after one week at room temperature and after 45 days at 45° C. The amounts are expressed in % by weight relative to the total weight of the composition.

| Phase | Ingredients | Formulation 5 (outside the invention) | Formulation 6 (invention) |
|---|---|---|---|
| A | Water | qsp 100 | qsp 100 |
|  | Glycerin | 5 | 5 |
|  | Disodium EDTA | 0.1 | 0.1 |
|  | Triethanolamine | 0.45 | 0.45 |
|  | Potassium Cetyl Phosphate (Amphisol K ®) | 1 | 1 |
| B | Isopropyl Lauroyl Sarcosinate (Eldew SL-205 ®) | 20 | 20 |
|  | Octocrylene (UVINUL N539 ®) | 10 | 10 |
|  | Butyl Methoxydibenzoylmethane (PARSOL 1789 ®) | 2 | 2 |
|  | (2Z)-2-cyano-N-(3-methoxypropyl)-2-{3-[(3-methoxypropyl)amino]cyclohex-2-en-1-ylidene}ethanamide | 2 | — |
|  | Compound (2) | — | 2 |
|  | Stearic Acid | 1.5 | 1.5 |
|  | Glyceryl Stearate (and) PEG-100 Stearate (Arlacel 165 ®) | 2.5 | 2.5 |
|  | Dimethicone | 0.5 | 0.5 |
|  | Cetyl Alcohol | 0.5 | 0.5 |
|  | Cetearyl Alcohol (and) Cetearyl Glucoside (Montanov 68 ®) | 2 | 2 |
|  | Preservatives | 1 | 1 |
| C | Isohexadecane | 1 | 1 |
|  | Xanthan Gum | 0.2 | 0.2 |
|  | Acrylates/C10-C30 Alkyl Acrylate crosspolymer (Pemulen TR1 ®) | 0.2 | 0.2 |
| D | Triethanolamine | 0.2 | 0.2 |
| SPF in vitro ($t_{1\,w}$) | | 44.6 ± 6.3 | 35.4 ± 3.1 |
| $UVA_{PPD}$ in vitro ($t_{1\,w}$) | | 47.9 ± 6.0 | 34.8 ± 3.1 |
| SPF in vitro ($t_{45\,d\,45°\,C.}$) | | 27.5 ± 4.8 | 35.8 ± 8.2 |
| $UVA_{PPD}$ in vitro ($t_{45\,d\,45°\,C.}$) | | 29.7 ± 5.2 | 36.2 ± 7.8 |

| Phase | Ingredients | Formulation 6 (invention) | Formulation 7 (outside the invention) | Formulation 8 (outside the invention) | Formulation 9 (outside the invention) |
|---|---|---|---|---|---|
| A | Water | qsp 100 | qsp 100 | qsp 100 | qsp 100 |
|  | Glycerin | 5 | 5 | 5 | 5 |
|  | Disodium EDTA | 0.1 | 0.1 | 0.1 | 0.1 |
|  | Triethanolamine | 0.45 | 0.45 | 0.45 | 0.45 |
|  | Potassium Cetyl Phosphate (Amphisol K ®) | 1 | 1 | 1 | 1 |
| B | Isopropyl Lauroyl Sarcosinate (Eldew SL-205 ®) | 20 | 20 | 30 | 30 |
|  | Octocrylene (UVINUL N539 ®) | 10 | 10 | — | — |
|  | Butyl | 2 | 2 | — | — |

-continued

|   | | | | | |
|---|---|---|---|---|---|
|   | Methoxydibenzoylmethane (PARSOL 1789 ®) | | | | |
|   | Compound (2) | 2 | — | 2 | — |
|   | MC11 of WO2008/090066 | — | 2 | — | 2 |
|   | Stearic acid | 1.5 | 1.5 | 1.5 | 1.5 |
|   | Glyceryl Stearate (and) PEG-100 Stearate (Arlacel 165 ®) | 2.5 | 2.5 | 2.5 | 2.5 |
|   | Dimethicone | 0.5 | 0.5 | 0.5 | 0.5 |
|   | Cetyl Alcohol | 0.5 | 0.5 | 0.5 | 0.5 |
|   | Cetearyl Alcohol (and) Cetearyl Glucoside (Montanov 68 ®) | 2 | 2 | 2 | 2 |
|   | Preservatives | 1 | 1 | 1 | 1 |
| C | Isohexadecane | 1 | 1 | 1 | 1 |
|   | Xanthan Gum | 0.2 | 0.2 | 0.2 | 0.2 |
|   | Acrylates/C10-C30 Alkyl Acrylate crosspolymer (Pemulen TR1 ®) | 0.2 | 0.2 | 0.2 | 0.2 |
| D | Triethanolamine | 0.2 | 0.2 | 0.2 | 0.2 |

Emulsion Preparation Method:

The aqueous phase A and oily phase B were prepared by mixing the starting materials with mechanical stirring at 80° C. Once the aqueous solution A and oily solution B were macroscopically homogeneous, the emulsion was prepared by introducing phase B into phase A with stirring using a rotor-stator homogenizer at a stirring speed of 4500 rpm for 20 minutes. Phases C and then D were then successively added, with continued stirring. The emulsion was finally cooled to room temperature before adding phase E. The final emulsion was characterized by drops between 1 μm and 20 μm in size.

In Vitro Protocol for Evaluating the Screening Efficacy

The sun protection factor (SPF) was determined according to the in vitro method described by B. L. Diffey in J. Soc. Cosmet. Chem. 40, 127-133 (1989). The measurements were carried out using a UV-1000S spectrophotometer from the company Labsphere. The "static in vitro protection factor (SPF)" value is extracted. Each composition is applied to a rough plate of PMMA in the form of a uniform and even deposit in a proportion of 1 mg/cm².

The in vitro $UVA_{PPD}$ index measurements were taken under the same conditions using a UV-1000S spectrophotometer from the company Labsphere. The "UV-$A_{PPD}$ index (persistent pigment darkening action spectrum)" value is extracted. Each composition is applied to a rough plate of PMMA, in the form of a uniform and even deposit in a proportion of 1 mg/cm².

Protocol for Evaluating the Absorbance Spectra of the Formulations

The absorbance spectra of the formulations were extracted from the mAF data as a function of the wavelength generated during the in vitro SPF measurement and the in vitro $UVA_{PPD}$ index measurement. The mAF values were then converted into absorbance values according to: Abs=log(mAF).

Absorbance of the Formulations Measured 24 Hours after Formulation

| Absorbance | Formulation 1 (outside the invention) | Formulation 2 (outside the invention) | Formulation 4 (invention) |
|---|---|---|---|
| Absorbance at 290 nm ($t_{24\,h}$) | 1.14 ± 0.07 | 1.10 ± 0.05 | 1.02 ± 0.12 |
| Absorbance at 320 nm ($t_{24\,h}$) | 1.18 ± 0.07 | 1.12 ± 0.06 | 1.06 ± 0.12 |
| Absorbance at 400 nm ($t_{24\,h}$) | 0.08 ± 0.01 | 0.19 ± 0.02 | 0.58 ± 0.05 |

Absorbance of the Formulations Measured after 10 Days at 60° C.

| Absorbance | Formulation 3 (outside the invention) | Formulation 4 (invention) |
|---|---|---|
| Absorbance at 290 nm (10 days, 60° C.) | 1.17 ± 0.4 | 1.09 ± 0.02 |
| Absorbance at 320 nm (10 days, 60° C.) | 1.19 ± 0.03 | 1.12 ± 0.02 |
| Absorbance at 400 nm (10 days, 60° C.) | 0.50 ± 0.01 | 0.62 ± 0.03 |

Conclusions

The absorbance values measured at 400 nm, 24 hours after formulation, show that for the same SPF and the same in vitro $UVA_{PPD}$ index, formulations 1 and 2 are less efficient than formulations 3 and 4.

The absorbance values measured at 400 nm, after 10 days at 60° C., show that for the same SPF and the same in vitro $UVA_{PPD}$ index, formulation 3 is less efficient than formulation 4 of the invention.

Absorbance of the Formulations 5 and 6 Measured after 1 Week of Storage at Room Temperature

| Absorbance | Formulation 5 (outside the invention) | Formulation 6 (invention) |
|---|---|---|
| Absorbance at 290 nm (1 W RT° C.) | 1.62 ± 0.05 | 1.52 ± 0.03 |
| Absorbance at 320 nm (1 W RT° C.) | 1.66 ± 0.04 | 1.55 ± 0.03 |
| Absorbance at 400 nm (1 W RT° C.) | 0.79 ± 0.02 | 0.91 ± 0.03 |

Absorbance of the Formulations 5 and 6 Measured after 45 Days at 45° C.

| Absorbance | Formulation 5 (outside the invention | Formulation 6 (invention) |
|---|---|---|
| Absorbance at 290 nm (45 d 45° C.) | 1.41 ± 0.08 | 1.50 ± 0.10 |
| Absorbance at 320 nm (45 d 45° C.) | 1.44 ± 0.08 | 1.53 ± 0.10 |
| Absorbance at 400 nm (45 d 45° C.) | 0.56 ± 0.02 | 0.84 ± 0.04 |

The SPF and UV-$A_{PPD}$ indexes in vitro measured on the formulations 5 and 6 show that the efficiency in UVB and UVA radiations was maintained in the time and in temperature for the formulation 6 according to the invention whereas the efficiency degraded for the formulation 5 (outside the invention).

Furthermore, the absorbance values measured at 400 nm on the formulations 5 and 6 after 1 week at room temperature show that formulation 5 was significantly less efficient in the long UVA than the formulation 6 according to the invention. This effect is more pronounced after 45 days of storage at 45° C.

Protocol for Evaluating the Color of the Formulations

The color of the formulations was evaluated after preparation of thin films on contrast map. The formulations were deposited within a circle of 2.2 cm of diameter and planed to obtain thicknesses of reproducible deposit. The colorimetric measures were then made by means of a spectro-colorimeter Minolta CM2600D in two points of the film. This operation is twice reproduced, which leads to 4 experimental values by formulation.

The results are expressed in the system (L*, has *, b*) in which L* represents the luminance, a* represents the red-green axis (−a*=green, +a*=red) and b* represents the yellow-blue axis (−b* blue, +b* yellow). So, a* and b* express the shade of the compound.

The difference of color ΔE* was calculated from the variations L*, a* et b* between the compound (2) and the compound MC11 with the following equation:

$$(\Delta E^*)^2 = (\Delta L1^*)^2 + (\Delta a^*)^2 + (\Delta b^*)^2$$

$\Delta L^* = L^*_{formulation\ with\ compound\ MC11} - L^*_{formulation\ with\ compound\ (2)}$ $\Delta a^* = a^*_{formulation\ with\ compound\ MC11} - a^*_{formulation\ with\ compound\ (2)}$ $\Delta b^* = b^*_{formulation\ with\ compound\ MC11} - b^*_{formulation\ with\ compound\ (2)}$ We consider that the difference of color between the two compounds is significant if ΔE*>2.

Colorimetric Measures on the Formulations 6 to 9

|  | Formulation 6 (invention) | Formulation 7 (outside the invention) | Formulation 8 (outside the invention) | Formulation 9 (outside the invention) |
|---|---|---|---|---|
| L* | 93.4 ± 0.7 | 93.1 ± 0.6 | 93.1 ± 0.6 | 93.0 ± 0.6 |
| a* | −7.1 ± 0.2 | −7.6 ± 0.1 | −5.08 ± 0.03 | −6.40 ± 0.05 |
| Δa* | | −0.5 | | −1.32 |
| b* | 18.2 ± 0.5 | 21.3 ± 0.7 | 12.0 ± 0.2 | 15.8 ± 0.2 |
| Δb* | | 3.1 | | 3.8 |
| ΔE* | | 3.2 | | 4.0 |

The colorimetry results on the examples 6 to 9 show that the formulation 6 with the compound (2) is significantly less yellow than the equivalent formulations 7, 8 and 9 with the compound MC11 of the application WO2008/090066.

B.2 Formulation Examples 10 to 14

The compound 2-ethoxyethyl (2Z)-cyano{3-[(3-methoxypropyl)amino]cyclohex-2-en-1-ylidene} (2) of the invention was compared with:
- the compound (2Z)-2-cyano-N-(3-methoxypropyl)-2-{3-[(3-methoxypropyl)amino]cyclohex-2-en-1-ylidene}-ethanamide according to Example A3 (outside the invention)
- the compound octyl-5-N,N-diethylamino-2-phenysulfonyl-2,4-pentadienoate (outside the invention),
- the merocyanine compound MC11 disclosed in the application WO2008/090066 (outside the invention).

Formulations 10 to 13 below were prepared; they were constructed such that the sum of the contents of oil and of liposoluble UV-screening agents remains constant. The content of the screening agents was adjusted so as to ensure the same level of UVB screening and also the same in vitro SPF, and also the same absorbance profile between 290 and 340 nm. For each of the formulations, the in vitro SPF, the in vitro $UVA_{PPD}$ index and the absorbance after 24 hours at room temperature and after 10 days at 60° C. were measured. The amounts are expressed as weight percentages relative to the total weight of the composition.

| Phase | Ingredients | Formulation 10 (outside the invention) | Formulation 11 (outside the invention) | Formulation 12 (outside the invention) | Formulation 13 (invention) |
|---|---|---|---|---|---|
| A | Water | qsp 100 | qsp 100 | qsp 100 | qsp 100 |
|  | Glycerol | 6 | 6 | 6 | 6 |
|  | Disodium EDTA | 0.1 | 0.1 | 0.1 | 0.1 |
|  | Triethanolamine | 3.15 | 3.15 | 3.15 | 3.15 |
|  | Phenylbenzimidazolesulfonic acid (Eusolex 232 ®) | 4 | 4 | 4 | 4 |
|  | Potassium cetyl phosphate (Amphisol K ®) | 1 | 1 | 1 | 1 |
| B | 2-Ethylphenyl benzoate (X-Tend 226 ®) | 26 | 25.7 | 25.5 | 25.3 |
|  | Butylmethoxydibenzoylmethane (Parsol 1789 ®) | 4 | 3.5 | 3.5 | 3.5 |
|  | Octyl 5-N,N-diethylamino-2-phenylsulfonyl-2,4-pentadienoate | — | 0.8 | — | — |
|  | (2Z)-2-cyano-N-(3-methoxypropyl)-2-{3-[(3-methoxypropyl)amino]cyclohex-2-en-1-ylidene}ethanamide | — | — | 1 | — |
|  | Compound (2) | — | — | — | 1.2 |
|  | Stearic acid | 1.5 | 1.5 | 1.5 | 1.5 |
|  | Glyceryl stearate (and) PEG-100 stearate (Arlacel 165 ®) | 1.5 | 1.5 | 1.5 | 1.5 |

-continued

| Phase | Ingredients | Formulation 10 (outside the invention) | Formulation 11 (outside the invention) | Formulation 12 (outside the invention) | Formulation 13 (invention) |
|---|---|---|---|---|---|
| | Dimethicone | 0.5 | 0.5 | 0.5 | 0.5 |
| | Preserving agents | 1.28 | 1.28 | 1.28 | 1.28 |
| C | Isohexadecane | 2 | 2 | 2 | 2 |
| | Xanthan gum | 0.1 | 0.1 | 0.1 | 0.1 |
| | Acrylates/C10-30 Alkyl Acrylate crosspolymer (Pemulen TR1 ®) | 0.25 | 0.25 | 0.25 | 0.25 |
| D | Triethanolamine | 0.25 | 0.25 | 0.25 | 0.25 |
| E | Alcohol | 2 | 2 | 2 | 2 |
| | in vitro SPF | 5.2 ± 0.6 | 4.6 ± 0.9 | 4.3 ± 0.7 | 5.4 ± 0.5 |
| | in vitro $UVA_{PPD}$ | 13.9 ± 2.8 | 14.7 ± 4.2 | 15.4 ± 4.1 | 21.3 ± 3.2 |

For the formulations 13 and 14 below, the content of the filters was constant in order to compare the performance of the compound (2) according to the invention to the one of the compound MC11 disclosed in the application WO2008/090066 (outside the invention) at the same content. The amounts are expressed as weight percentages relative to the total weight of the composition.

| Phase | Ingrédients | Formulation 13 (invention) | Formulation 14 (outside the invention) |
|---|---|---|---|
| A | Water | qsp 100 | qsp 100 |
| | Glycerin | 6 | 6 |
| | Disodium EDTA | 0.1 | 0.1 |
| | Triethanolamine | 3.15 | 3.15 |
| | Phenylbenzimidazole Sulfonic Acid (Eusolex 232 ®) | 4 | 4 |
| | Potassium Cetyl Phosphate (Amphisol K ®) | 1 | 1 |
| B | 2-Ethylphenyle benzoate (X-Tend 226 ®) | 25.3 | 25.3 |
| | Butyl Methoxydibenzoylmethane (PARSOL 1789 ®) | 3.5 | 3.5 |
| | Compound (2) | 1.2 | — |
| | MC11 of WO2008/090066 | — | 1.2 |
| | Stearic Acid | 1.5 | 1.5 |
| | Glyceryl Stearate (and) PEG-100 Stearate (Arlacel 165 ®) | 1.5 | 1.5 |
| | Dimethicone | 0.5 | 0.5 |
| | Preservatives | 1.28 | 1.28 |
| C | Isohexadecane | 2 | 2 |
| | Xanthan gum | 0.1 | 0.1 |
| | Acrylates/C10-30 Alkyl Acrylate crosspolymer (Pemulen TR1 ®) | 0.25 | 0.25 |
| D | Triethanolamine | 0.25 | 0.25 |
| E | Alcohol | 2 | 2 |

Emulsions 10 to 14 were prepared according to the same preparation mode as for Examples 1 to 9.

The in vitro SPF and $UVA_{PPD}$ index values were measured under the same conditions indicated previously.

Protocol for Evaluating the Absorbance Spectra of the Formulations

The absorbance spectra of the formulations were extracted from the mAF data as a function of the wavelength generated during the in vitro SPF measurement and the in vitro $UVA_{PPD}$ index measurement. The mAF values were then converted into absorbance values according to: Abs=log(mAF).

Absorbance of the Formulations Measured 24 Hours after Formulation

| Absorbance | Formulation 10 (outside the invention) | Formulation 11 (outside the invention) | Formulation 12 (outside the invention) | Formulation 13 (invention) |
|---|---|---|---|---|
| Absorbance at 290 nm ($t_{24\,h}$) | 0.70 ± 0.06 | 0.64 ± 0.09 | 0.61 ± 0.08 | 0.73 ± 0.04 |
| Absorbance at 320 nm ($t_{24\,h}$) | 0.86 ± 0.06 | 0.78 ± 0.11 | 0.77 ± 0.10 | 0.88 ± 0.05 |
| Absorbance at 400 nm ($t_{24\,h}$) | 0.08 ± 0.01 | 0.15 ± 0.03 | 0.44 ± 0.05 | 0.65 ± 0.03 |

Conclusions

The in vitro $UVA_{PPD}$ value and the absorbance value at 400 nm measured 24 hours after formulation show that for the same in vitro SPF and a similar absorbance profile in the UVB range (from 290 to 320 nm), the phenylbenzimidazolesulfonic acid/butylmethoxydibenzoylmethane combination (Formulation 10) is significantly less protective than the phenylbenzimidazolesulfonic acid/butylmethoxydibenzoylmethane/merocyanine combination of the invention (Formulation 13).

The phenylbenzimidazolesulfonic acid/phenylbenzimidazolesulfonic acid/compound 2 combination of the invention (Formulation 13) differs from the phenylbenzimidazolesulfonic acid/phenylbenzimidazolesulfonic acid/octyl 5-N,N-diethylamino-2-phenysulfonyl-2,4-pentadienoate combination (Formation 11) and the phenylbenzimidazolesulfonic acid/phenylbenzimidazolesulfonic acid/(2Z)-2-cyano-N-(3-methoxypropyl)-2-{3-[(3-methoxypropyl)amino]cyclohex-2-en-1-ylidene}ethanamide combination (Formulation 12) by a significantly higher absorbance at 400 nm measured 24 hours after formulation for comparable in vitro SPF and $UVA$-$_{PPD}$ values.

Colorimetric Measures on the Formulations 13 and 14

The colorimetric measurements on the formulations 13 and 14 were made in the same conditions as previously indicated.

| | Formulation 13 (invention) | Formulation 14 (outside the invention) |
|---|---|---|
| L* | 93.0 ± 0.7 | 93.6 ± 0.6 |
| a* | −4.72 ± 0.03 | −6.4 ± 0.2 |
| Δa* | −1.7 | |
| b* | 12.8 ± 0.2 | 15.9 ± 0.5 |
| Δb* | 3.1 | |
| ΔE* | 3.6 | |

The colorimetry results on the examples 13 and 14 show that the formulation 13 with the compound (2) is significantly less yellow than the equivalent formulation 14 with the compound MC11 of the application WO2008/090066.

B.3 Formulation Examples 15 to 21

The compound 2-ethoxyethyl (2Z)-cyano{3-[(3-methoxypropyl)amino]cyclohex-2-en-1-ylidene} (2) of the invention was compared with:
- the compound (2Z)-2-cyano-N-(3-methoxypropyl)-2-{3-[(3-methoxypropyl)amino]cyclohex-2-en-1-ylidene}ethanamide according to Example A3 (outside the invention)
- the compound octyl-5-N,N-diethylamino-2-phenysulfonyl-2,4-pentadienoate (outside the invention)

Formulations 15 to 18 below were prepared; they were constructed such that the sum of the contents of oil and of liposoluble UV-screening agents remains constant. The content of the screening agents was adjusted so as to ensure the same level of UVB screening and also the same in vitro SPF, and also the same absorbance profile between 290 and 340 nm. For each of the formulations, the in vitro SPF, the in vitro $UVA_{PPD}$ index and the absorbance after 24 hours at room temperature were measured.

The formulations 19 to 21 below were prepared. The content of the filters was constant in order to compare the performance of the compound (2) to the one of (2Z)-2-cyano-N-(3-methoxy-propyl)-2-{3-[(3-meth-oxypropyl)amino]cyclohex-2-en-1-ylidene}-ethanamide according to example A3 (outside the invention) and to the one of the compound MC11 disclosed in the application WO2008/090066 (outside the invention) at the same content. For the formulations 20 and 21, SPF, $UVA_{PPD}$ index and absorbance were measured after one week at room temperature and after 45 days at 45° C. The amounts are expressed in % by weight relative to the total weight of the composition.

| Phase | Ingredients | Formulation 19 (outside the invention) | Formulation 20 (invention) |
|---|---|---|---|
| A | Water | qsp 100 | qsp 100 |
|   | Glycerin | 5 | 5 |
|   | Disodium EDTA | 0.1 | 0.1 |
|   | Triethanolamine | 0.45 | 0.45 |
|   | Potassium Cetyl Phosphate (Amphisol K ®) | 1 | 1 |
| B | Isopropyl Lauroyl Sarcosinate (Eldew SL-205 ®) | 30 | 30 |
|   | Drometrizole Trisiloxane (Mexoryl XL) | 5 | 5 |
|   | Ethylhexyl Triazone (Uvinul T150 ®) | 1.5 | 1.5 |
|   | (2Z)-2-cyano-N-(3-methoxypropyl)-2-{3-[(3-methoxypropyl)amino]cyclohex-2-en-1-ylidene}ethanamide | 2 | — |
|   | Compound (2) | — | 2 |

| Phase | Ingredients | Formulation 15 (outside the invention) | Formulation 16 (outside the invention) | Formulation 17 (outside the invention) | Formulation 18 (invention) |
|---|---|---|---|---|---|
| A | Water | qsp 100 | qsp 100 | qsp 100 | qsp 100 |
|   | Glycerin | 6 | 6 | 6 | 6 |
|   | Disodium EDTA | 0.1 | 0.1 | 0.1 | 0.1 |
|   | Potassium cetyl phosphate (Amphisol K ®) | 1 | 1 | 1 | 1 |
|   | Triethanolamine | qs pH 8.5 | qs pH 8.5 | qs pH 8.5 | qs pH 8.5 |
|   | Terephthalylidenedicamphorsulfonic acid, (Mexoryl SX ®) (% active material) | 5.2 | 4.8 | 4.8 | 4.8 |
| B | 2-Ethylphenyl benzoate (X-Tend 226 ®) | 18.8 | 17.5 | 17 | 16.8 |
|   | Ethylhexyl triazone (Uvinul T150 ®) | 1.2 | 1.2 | 1.2 | 1.2 |
|   | Octyl 5-N,N-diethylamino-2-phenylsulfonyl-2,4-pentadienoate | — | 1.3 | — | — |
|   | (2Z)-2-cyano-N-(3-methoxypropyl)-2-{3-[(3-methoxypropyl)amino]cyclohex-2-en-1-ylidene}ethanamide | — | — | 1.8 | — |
|   | Compound (2) | — | — | — | 2 |
|   | Stearic acid | 1.5 | 1.5 | 1.5 | 1.5 |
|   | Glyceryl stearate (and) PEG-100 stearate (Arlacel 165 ®) | 1.5 | 1.5 | 1.5 | 1.5 |
|   | Dimethicone | 0.5 | 0.5 | 0.5 | 0.5 |
|   | Preservatives | 1.28 | 1.28 | 1.28 | 1.28 |
| C | Isohexadecane | 2 | 2 | 2 | 2 |
|   | Xanthan gum | 0.1 | 0.1 | 0.1 | 0.1 |
|   | Acrylates/C10-30 alkyl acrylate crosspolymer (Pemulen TR1 ®) | 0.25 | 0.25 | 0.25 | 0.25 |
| D | Triethanolamine | 0.25 | 0.25 | 0.25 | 0.25 |
| E | Alcohol | 2 | 2 | 2 | 2 |
|   | in vitro SPF | 7.2 ± 0.4 | 9.0 ± 1.4 | 7.9 ± 1 | 8.1 ± 0.9 |
|   | in vitro $UVA_{PPD}$ | 2.2 ± 0.1 | 6.6 ± 0.8 | 4.9 ± 0.6 | 5.3 ± 0.5 |

-continued

| | | | |
|---|---|---|---|
| | Stearic acid | 1.5 | 1.5 |
| | Glyceryl Stearate (and) PEG-100 Stearate (Arlacel 165 ®) | 2.5 | 2.5 |
| | Dimethicone | 0.5 | 0.5 |
| | Cetyl Alcohol | 0.5 | 0.5 |
| | Cetearyl Alcohol (and) Cetearyl Glucoside (Montanov 68 ®) | 2 | 2 |
| | Preservatives | 1 | 1 |
| C | Isohexadecane | 1 | 1 |
| | Xanthan gum | 0.2 | 0.2 |
| | Acrylates/C10-C30 Alkyl Acrylate crosspolymer (Pemulen TR1 ®) | 0.2 | 0.2 |
| D | Triethanolamine | 0.2 | 0.2 |
| | SPF in vitro ($t_{1w}$) | 33.6 ± 5.0 | 26.5 ± 5.0 |
| | $UVA_{PPD}$ in vitro ($t_{1w}$) | 25.9 ± 3.2 | 17.6 ± 3.3 |
| | SPF in vitro ($t_{45\,d\,45°\,C.}$) | 32.2 ± 7.0 | 28.4 ± 2.7 |
| | $UVA_{PPD}$ in vitro ($t_{45\,d\,45°\,C.}$) | 19.2 ± 2.5 | 18.6 ± 1.6 |

| Phase | Ingrédients | Formule 20 (invention) | Formule 21 (outside the invention) |
|---|---|---|---|
| A | Water | qsp 100 | qsp 100 |
| | Glycerin | 5 | 5 |
| | Disodium EDTA | 0.1 | 0.1 |
| | Triethanolamine | 0.45 | 0.45 |
| | Potassium Cetyl Phosphate(Amphisol K ®) | 1 | 1 |
| B | Isopropyl Lauroyl Sarcosinate (Eldew SL-205 ®) | 30 | 30 |
| | Drometrizole Trisiloxane (Mexoryl XL) | 5 | 5 |
| | Ethylhexyl Triazone (Uvinul T150 ®) | 1.5 | 1.5 |
| | Compound (2) | 2 | — |
| | MC11 of WO2008/090066 | — | 2 |
| | Stearic acid | 1.5 | 1.5 |
| | Glyceryl Stearate (and) PEG-100 Stearate (Arlacel 165 ®) | 2.5 | 2.5 |
| | Dimethicone | 0.5 | 0.5 |
| | Cetyl Alcohol | 0.5 | 0.5 |
| | Cetearyl Alcohol (and) Cetearyl Glucoside (Montanov 68 ®) | 2 | 2 |
| | Preservatives | 1 | 1 |
| C | Isohexadecane | 1 | 1 |
| | Xanthan Gum | 0.2 | 0.2 |
| | Acrylates/C10-C30 Alkyl Acrylate crosspolymer (Pemulen TR1 ®) | 0.2 | 0.2 |
| D | Triéthanolamine | 0.2 | 0.2 |

Emulsions 15 to 21 were prepared according to the same preparation mode as for Examples 1 to 4.

The in vitro SPF and $UVA_{PPD}$ index values were measured under the same conditions indicated previously.

Protocol for Evaluating the Absorbance Spectra of the Formulations

The absorbance spectra of the formulations were extracted from the mAF data as a function of the wavelength generated during the in vitro SPF measurement and the in vitro $UVA_{PPD}$ index measurement. The mAF values were then converted into absorbance values according to: Abs=log(mAF).

Absorbance of the Formulations 15 to 18 Measured 24 Hours after Formulation

| Absorbance | Formulation 15 (outside the invention) | Formulation 16 (outside the invention) | Formulation 17 (outside the invention) | Formulation 18 (invention) |
|---|---|---|---|---|
| Absorbance at 290 nm ($t_{24\,h}$) | 0.68 ± 0.02 | 0.72 ± 0.05 | 0.67 ± 0.04 | 0.68 ± 0.04 |
| Absorbance at 320 nm ($t_{24\,h}$) | 0.87 ± 0.02 | 0.95 ± 0.07 | 0.89 ± 0.05 | 0.91 ± 0.05 |
| Absorbance at 400 nm ($t_{24\,h}$) | 0.02 ± 0.01 | 0.18 ± 0.01 | 0.59 ± 0.05 | 0.74 ± 0.05 |

Conclusions

The absorbance values and the in vitro $UVA_{PPD}$ values measured at $t_{24h}$ show that for the same absorbance profile in the UVB range and for the same in vitro SPF, formulation 15 without merocyanine is significantly less efficient than formulation 18 in terms of protection against UVA.

The absorbance values measured at 400 nm at $t_{24h}$ also show that for the same absorbance profile in the UVB range, for the same in vitro SPF and the same in vitro $UVA_{PPD}$ index, formulations 16 and 17 containing a merocyanine outside the invention (respectively, the compounds octyl 5-N,N-diethylamino-2-phenylsulfonyl-2,4-pentadienoate or (2Z)-2-cyano-N-(3-methoxypropyl)-2-{3-[(3-methoxypropyl)amino]cyclohex-2-en-1-ylidene}ethanamide) are significantly less efficient in terms of protection against long UVA than formulation 18 containing the compound 2-ethoxyethyl (2Z)-cyano{3-[(3-methoxypropyl)amino]cyclohex-2-en-1-ylidene}ethanoate (2) of the invention.

Absorbance of Formulations 19 Et 20 Measured after One Week of Storage at Room Temperature

| Absorbance | Formule 19 (hors invention) | Formule 20 (invention) |
|---|---|---|
| Absorbance at 290 nm (1 W T ° C.) | 1.14 ± 0.05 | 1.06 ± 0.06 |
| Absorbance at 320 nm (1 W T ° C.) | 1.61 ± 0.08 | 1.49 ± 0.08 |
| Absorbance at 400 nm (1 W T ° C.) | 0.73 ± 0.04 | 0.83 ± 0.07 |

Absorbance of Formulations 19 Et 20 Measured after 45 Days at 45° C.

| Absorbance | Formule 19 (hors invention) | Formule 20 (invention) |
|---|---|---|
| Absorbance at 290 nm (45 d 45° C.) | 1.16 ± 0.06 | 1.10 ± 0.03 |
| Absorbance at 320 nm (45 d 45° C.) | 1.55 ± 0.10 | 1.50 ± 0.04 |
| Absorbance at 400 nm (45 d 45° C.) | 0.52 ± 0.02 | 0.79 ± 0.03 |

The in vitro $UV-A_{PPD}$ indexes measured on the formulations 19 and 20 show that the efficiency in UVA radiations was maintained in the time and in temperature for the formulation 20 according to the invention whereas the efficiency degraded for the formulation 19 (outside the invention).

Furthermore, the absorbance values measured at 400 nm on the formulations 19 and 20 after 45 days of storage at 45° C. show that formulation 19 was significantly less efficient in the long UVA than the formulation 20 according to the invention.

Colorimetric Measures on the Formulations 20 and 21

The colorimetric measurements on the formulations 20 and 21 were made in the same conditions as previously indicated.

|   | Formulation 20 (invention) | Formulation 21 (outside the invention) |
|---|---|---|
| L* | 93.3 ± 0.7 | 92.9 ± 0.7 |
| a* | −4.99 ± 0.08 | −6.34 ± 0.15 |
| Δa* |   | −1.35 |
| b* | 11.9 ± 0.2 | 17.0 ± 0.5 |
| Δb* |   | 5.1 |
| ΔE* |   | 5.3 |

The colorimetry results on the examples 20 and 21 show that the formulation 20 with the compound (2) is significantly less yellow than the equivalent formulation 21 with the compound MC11 of the application WO2008/090066.

The invention claimed is:

1. A cosmetic or dermatological composition comprising, in a physiologically acceptable support:
   a) at least one oily phase and
   b) 0.1% to 10% by weight relative to the total weight of the composition of at least one merocyanine compound chosen from the following compounds, and the E/E- or E/Z-geometrical isomer forms thereof:

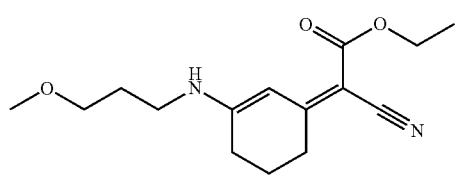

ethyl (2Z)-cyano{3-[(3-methoxypropyl)amino]cyclohex-2-en-1-ylidene}enthanoate

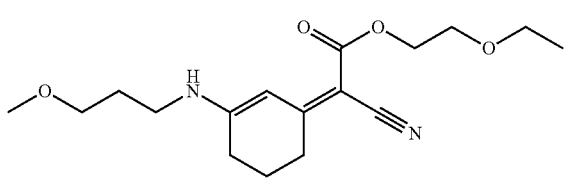

2-ethoxyethyl (2Z)-cyano{3-[(3-methoxypropyl)amino]cyclohex-2-en-1-ylidene}ethanoate

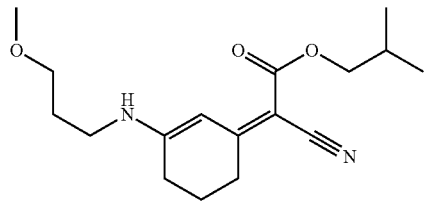

2-methylpropyl (2Z)-cyano{3-[(3-methoxypropyl)amino]cyclohex-2-en-1-ylidene}ethanoate

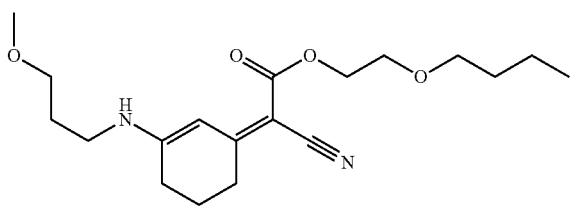

2-butoxyethyl (2Z)-cyano{3-[(3-methoxypropyl)amino]cyclohex-2-en-1-ylidene}ethanoate

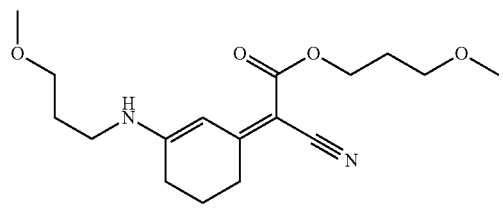

3-methoxypropyl (2Z)-cyano{3-[(3-methoxypropyl)amino]cyclohex-2-en-1-ylidene}ethanoate

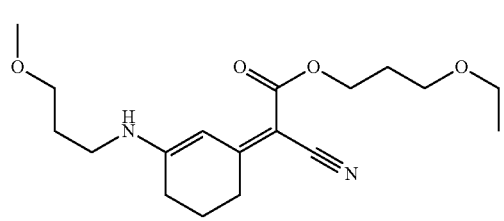

3-ethoxypropyl (2Z)-cyano-{3-[(3-methoxypropyl)amino]cyclohex-2-en-1-ylidene}ethanoate c) at least one organic UVB-screening agent chosen from:
   i) 0.1% to 40% by weight relative to the total weight of the composition of a liquid lipophilic organic UVB-screening agent
   ii) 0.1% to 15% by weight relative to the total weight of the composition of a hydrophilic organic UVB-screening agent
   iii) 0.1% to 30% by weight relative to the total weight of the composition of a triazine UVB-screening agent and
   iv) mixtures thereof; and
d) at least one organic UVA-screening agent other than the said merocyanine compound;

when the said UVB-screening agent is liquid and lipophilic, the said composition contains less than 2% by weight of cyclohexasiloxane relative to the total weight of the composition.

2. The composition according to claim 1, which the merocyanine compound(s) of formula (1) are chosen from the following compounds, and the E/E- or E/Z-geometrical isomer forms thereof:

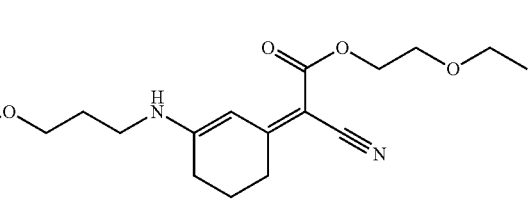

2-ethoxyethyl (2Z)-cyano{3-[(3-methoxypropyl)amino]cyclohex-2-en-1-ylidene}ethanoate -continued

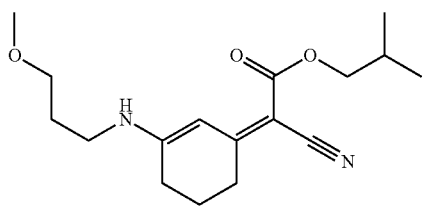

2-methylpropyl (2Z)-cyano{3-[(3-methoxypropyl)amino]cyclohex-2-en-1-ylidene}ethanoate

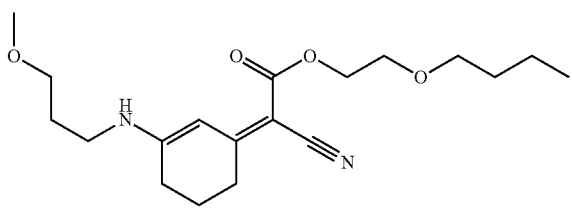

2-butoxyethyl (2Z)-cyano{3-[(3-methoxypropyl)amino]cyclohex-2-en-1-ylidene}ethanoate

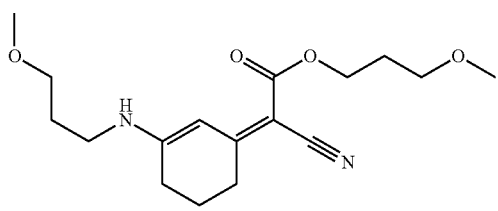

3-methoxypropyl (2Z)-cyano{3-[(3-methoxypropyl)amino]cyclohex-2-en-1-ylidene}ethanoate

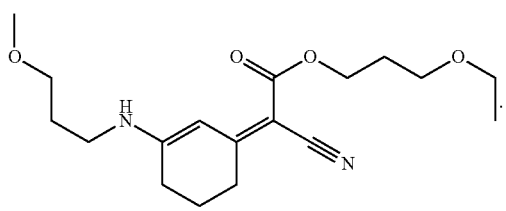

3-ethoxypropyl (2Z)-cyano{3-[(3-methoxypropyl)amino]cyclohex-2-en-1-ylidene}ethanoate 3. The composition according to claim 2, which the merocyanine compound is 2-ethoxyethyl (2Z)-cyano{3-[(3-methoxypropyl)amino]cyclohex-2-en-1-ylidene}ethanoate (2) in its E/Z geometrical configuration having the following structure:

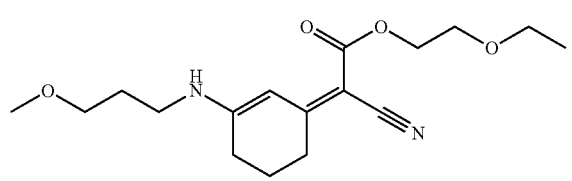 [SMILES: CCOCCOC(=O)/C(C#N)=C1\C=C(NCCCOC)CCC1]

and/or in its E/E geometrical configuration having the following structure:

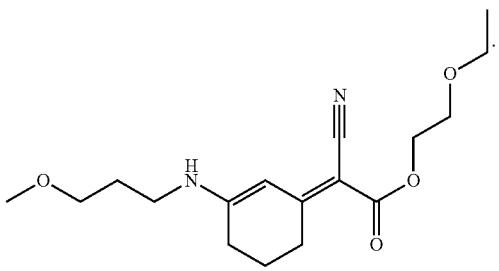 [SMILES: CCOCCOC(=O)/C(C#N)=C1/C=C(NCCCOC)CCC1]

4. A cosmetic or dermatological composition comprising, in a physiologically acceptable support:
   a) at least one oily phase and
   b) 0.1% to 10% by weight relative to the total weight of the composition of at least one merocyanine compound of formula (1) defined hereinbelow or an E/E- or E/Z-geometrical isomer form thereof:

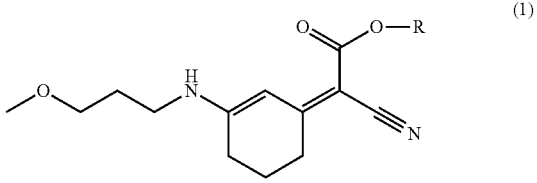

(1)

in which:
   R is selected from the group consisting of a $C_1$-$C_{22}$ alkyl group, and
   wherein said groups are optionally interrupted with one or more O; and
   c) at least one organic UVB-screening agent chosen from:
      i) 0.1% to 40% by weight relative to the total weight of the composition of a liquid lipophilic organic UVB-screening agent
      ii) 0.1% to 15% by weight relative to the total weight of the composition of a hydrophilic organic UVB-screening agent
      iii) 0.1% to 30% by weight relative to the total weight of the composition of a triazine UVB-screening agent and
      iv) mixtures thereof; and
   d) at least one organic UVA-screening agent other than the said merocyanine compound;
when the said UVB-screening agent is liquid and lipophilic, the said composition contains less than 2% by weight of cyclohexasiloxane relative to the total weight of the composition.

5. The composition according to claim 4, which the merocyanine compound(s) of formula (1) are chosen from those in which:
   R is a $C_1$-$C_{22}$ alkyl, which is optionally interrupted with one or more O.

6. The composition according to claim 4, in which the liquid organic UVB-screening agent(s) are chosen from:
   liquid lipophilic β,β-diphenylacrylate compounds
   liquid lipophilic salicylate compounds
   liquid lipophilic cinnamate compounds
   and mixtures thereof.

7. The composition according to claim 6, in which the liquid organic UVB-screening agent(s) are chosen from:
Octocrylene
Homosalate,
Ethylhexyl salicylate
Ethylhexyl methoxycinnamate, and mixtures thereof.

8. The composition according to claim 7, in which the liquid organic UVB-screening agent(s) are chosen from:
Octocrylene
Ethylhexyl salicylate, and mixtures thereof.

9. The composition according to claim 4, which the hydrophilic UVB-screening agent(s) are chosen from:
hydrophilic cinnamic derivatives;
hydrophilic benzylidenecamphor compounds;
hydrophilic phenylbenzimidazole compounds;
hydrophilic p-aminobenzoic (PABA) compounds;
hydrophilic salicylic compounds;
mixtures thereof.

10. The composition according to claim 9, in which the hydrophilic UVB-screening agent(s) are chosen from hydrophilic phenylbenzimidazole compounds.

11. The composition according to claim 4, which the triazine UVB-screening agent(s) are chosen from the 1,3,5-triazine derivatives of formula (I) below

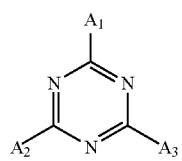
(I)

in which the radicals $A_1$, $A_2$ and $A_3$, which may be identical or different, are chosen from the groups of formula (II):

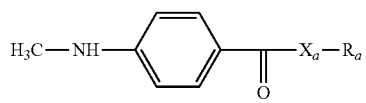
(II)

in which:
$X_a$, which may be identical or different, represent oxygen or an —NH— radical;
$R_a$, which may be identical or different, are chosen from a linear or branched $C_1$-$C_{18}$ alkyl radical; a $C_5$-$C_{12}$ cycloalkyl radical optionally substituted with one or more $C_1$-$C_4$ alkyl radicals;
a polyoxyethylenated hydrocarbon-based radical comprising from 1 to 6 ethylene oxide units and in which the end OH group is methylated; a radical of formula (III), (IV) or (V) below:

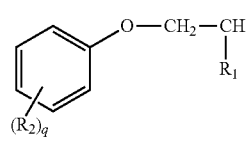
(III)

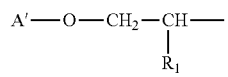
(IV)

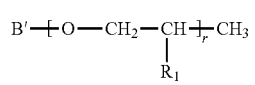
(V)

in which:
$R_1$ is hydrogen or a methyl radical;
$R_2$ is a $C_1$-$C_9$ alkyl radical;
q is an integer ranging from 0 to 3;
r is an integer ranging from 1 to 10;
A' is a $C_4$-$C_8$ alkyl radical or a $C_5$-$C_8$ cycloalkyl radical;
B' is chosen from: a linear or branched $C_1$-$C_8$ alkyl radical; a $C_5$-$C_8$ cycloalkyl radical; an aryl radical optionally substituted with one or more $C_1$-$C_4$ alkyl radicals;

it being understood that when $A_1$, $A_2$ and $A_3$ are identical and $X_a$ denotes an oxygen atom, then $R_a$ represents a branched $C_6$-$C_{18}$ alkyl radical.

12. The composition according to claim 11, in which the triazine UVB-screening agent of formula (I) is chosen from the following compounds:

2-[(p-(tert-butylamido)anilino]-4,6-bis[(p-(2'-ethylhexyl-1'-oxycarbonyl)anilino]-1,3,5-triazine corresponding to the following formula:

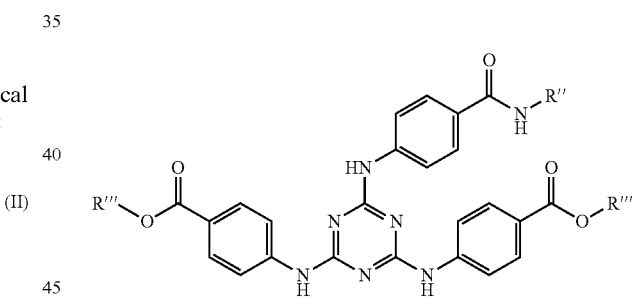

in which R'" denotes a 2-ethylhexyl radical and R" denotes a tert-butyl radical;

2,4,6-tris[p-(2'-ethylhexyl-1'-oxycarbonyl)anilino]-1,3,5-triazine corresponding to the following formula:

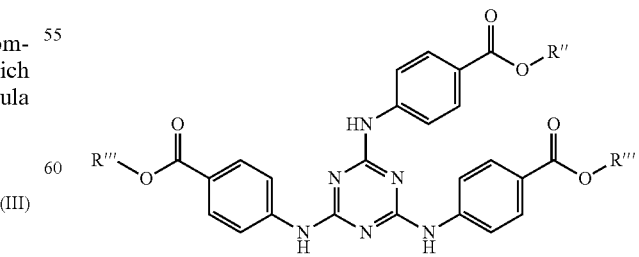

in which R'" denotes a 2-ethylhexyl radical
mixtures thereof.

13. The composition according to claim 4, which the triazine UVB-screening agent(s) are chosen from the silicone triazines of formula (VI) below, or a tautomeric form thereof $$(D)-(Si)-O_{(3-a)/2}$$
$$\underset{(R^1)_a}{|}$$
(VI)

in which:
R$^1$, which may be identical or different, represent a linear or branched $C_1$-$C_{30}$ alkyl radical which is optionally halogenated or unsaturated, a $C_6$-$C_{12}$ aryl radical, a $C_1$-$C_{10}$ alkoxy radical, a hydroxyl radical or the trimethylsilyloxy group;
a=1 to 3; in addition to the units of formula $A(Si)(R)_a(O)_{(3-a)/2}$,
the group (D) denotes an s-triazine compound of formula (VII) below:

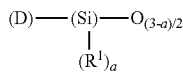

(VII)

in which:
X represents —O— or —NR$_{10}$-, with R$_{10}$ representing hydrogen or a $C_1$-$C_5$ alkyl radical,
R$_8$ represents a linear or branched $C_1$-$C_{30}$ alkyl radical which is optionally unsaturated and which optionally comprises a silicon atom, a $C_5$-$C_{20}$ cycloalkyl group, optionally substituted with 1 to 3 linear or branched $C_1$-$C_4$ alkyl radicals, the group —(CH$_2$CHR$_{10}$—O)$_m$R$_{11}$ or the group —CH$_2$—CH(OH)—CH$_2$—O—R$_{12}$,
R$_9$, which may be identical or different, represent a hydroxyl radical, a linear or branched $C_1$-$C_8$ alkyl radical or a $C_1$-$C_8$ alkoxy radical, and wherein two adjacent R$_2$ groups on the same aromatic nucleus may together form an alkylidenedioxy group in which the alkylidene group contains 1 or 2 carbon atoms,
R$_{10}$ represents hydrogen or methyl; wherein the group (C=O)XR$_8$ can be in the ortho, meta or para position relative to the amino group,
R$_{11}$ represents hydrogen or a $C_1$-$C_8$ alkyl group,
R$_{12}$ represent hydrogen or a $C_4$-$C_8$ alkyl group,
m is an integer ranging from 2 to 20,
n=0 to 2,
A is a divalent radical chosen from methylene or a group corresponding to one of the formulae (VIII), (IX), (X) or (XI) below:

$$—(Z)—CH—CH_2—$$
$$\underset{W}{|}$$
(VIII)

$$—(Z)—CH—$$
$$\underset{CH_3}{|}$$
(IX)

$$—(Z)—CH=CH—$$
(X)

$$—(Z)—C—$$
$$\underset{CH_2}{\parallel}$$
(XI)

in which:
Z is a saturated or unsaturated, linear or branched $C_1$-$C_{10}$ alkylene diradical, optionally substituted with a hydroxyl radical or oxygen atoms and optionally containing an amino group;
W represents a hydrogen atom, a hydroxyl radical or a linear or branched, saturated or unsaturated $C_1$-$C_8$ alkyl radical; the said organosiloxane compound of formula (VI) may also comprise units of formula: $(R^1)_b$—(Si)(O)$_{(4-b)/2}$ in which R$^1$ has the same meaning as in formula (VI), b=1, 2 or 3.

14. The composition according to claim 13, in which the triazine compounds of formula (VI) are represented by formula (VIa), (VIb) or (VIc) below:

$$(B)-\underset{R_{13}}{\overset{R_{13}}{Si}}-O\underset{R_{13}}{\overset{R_{13}}{+Si-O+}}_r\underset{(D)}{\overset{R_{13}}{+Si-O+}}_s\underset{R_{13}}{\overset{R_7}{Si}}-(B)$$
(VIa)

$$[-O-\underset{R_{13}}{\overset{R_{13}}{Si-}}]_t[-O-\underset{(D)}{\overset{R_{13}}{Si-}}]_u$$
(VIb)

(D)—Si(R$_{14}$)$_3$
(VIc)

in which:
(D) denotes an s-triazine compound of formula (VII) below:

(VII)

in which:
X represents —O— or —NR$_{10}$—, with R$_{10}$ representing hydrogen or a $C_1$-$C_5$ alkyl radical,
R$_8$ represents a linear or branched $C_1$-$C_{30}$ alkyl radical which is optionally unsaturated and which may comprise a silicon atom, a $C_5$-$C_{20}$ cycloalkyl group, optionally substituted with 1 to 3 linear or branched $C_1$-$C_4$ alkyl radicals, the group —(CH$_2$CHR$_{10}$—O)$_m$R$_{11}$ or the group —CH$_2$—CH(OH)—CH$_2$—O—R$_{12}$, R$_9$, which may be identical or different, represent a hydroxyl radical, a linear or branched C$_1$-C$_8$ alkyl radical or a C$_1$-C$_8$ alkoxy radical, it being possible for two adjacent R$_2$ groups on the same aromatic nucleus together to form an alkylidenedioxy group in which the alkylidene group contains 1 or 2 carbon atoms, R$_{10}$ represents hydrogen or methyl; it being possible for the group (C=O)XR$_8$ to be in the ortho, meta or para position relative to the amino group, R$_{11}$ represents hydrogen or a C$_1$-C$_8$ alkyl group, R$_{12}$ represent hydrogen or a C$_4$-C$_8$ alkyl group, m is an integer ranging from 2 to 20, n=0 to 2, A is a divalent radical chosen from methylene or a group corresponding to one of the formulae (VIII), (IX), (X) or (XI) below:

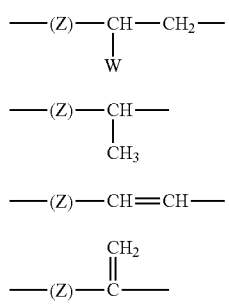

in which:

Z is a saturated or unsaturated, linear or branched C$_1$-C$_{10}$ alkylene diradical, optionally substituted with a hydroxyl radical or oxygen atoms and optionally containing an amino group;

W represents a hydrogen atom, a hydroxyl radical or a linear or branched, saturated or unsaturated C$_1$-C$_8$ alkyl radical; the said organosiloxane compound of formula (VI) may also comprise units of formula: (R$^1$)$_b$—(Si)(O)$_{(4-b)/2}$ in which R$^1$ has the same meaning as in formula (VI), b=1, 2 or 3;

R$_{13}$, which may be identical or different, are chosen from linear or branched C$_1$-C$_{20}$ alkyl, phenyl, 3,3,3-trifluoropropyl and trimethylsilyloxy radicals or the hydroxyl radical, R$_{14}$, which may be identical or different, are chosen from linear or branched C$_1$-C$_{20}$ alkyl and alkenyl radicals, hydroxyl radicals or phenyl radicals, (B), which may be identical or different, are chosen from the R$_{13}$ radicals and the (D) radical, r is an integer between 0 and 200 inclusive, s is an integer ranging from 0 to 50 and, if s=0, at least one of the two (B) symbols denotes (D), u is an integer ranging from 1 to 10, t is an integer ranging from 0 to 10, it being understood that t+u is equal to or greater than 3, and the tautomeric forms thereof.

15. The composition according to claim 14, in which the triazine compound of formula (VI) is the compound 2,4-bis(n-butyl 4'-diylaminobenzoate)-6-{[1,3,3,3-tetramethyl-1-[(trimethylsilyl)oxy]disiloxanyl]propyl-3-ylamino}-s-triazine of structure (VI$_2$):

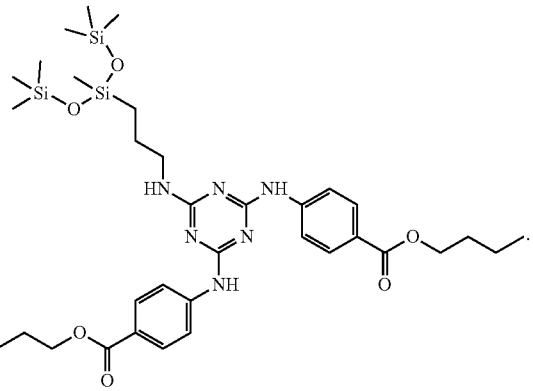

16. The composition according to claim 4, in which the organic UVA-screening agent(s) are chosen from:

organic UVA-screening agents of the type (A) which are capable of exclusively absorbing UV rays between 320 and 400 nm, organic UVA-screening agents of the type (B) which are capable of simultaneously absorbing UV rays between 280 and 320 nm and those between 320 and 400 nm, and mixtures thereof.

17. The composition according to claim 16, in which the organic UVA-screening agents of the type (A) are chosen from dibenzoylmethane compounds; amino-substituted hydroxybenzophenone compounds; anthranilic compounds; benzylidenecamphor compounds; 4,4-diarylbutadiene compounds; bis-benzazolyl compounds; and mixtures thereof.

18. The composition according to claim 17, in which the organic UVA-screening agents of the type (A) are chosen from the following compounds:

butylmethoxydibenzoylmethane;

n-hexyl 2-(4-diethylamino-2-hydroxybenzoyl)benzoate;

terephthalylidenedicamphorsulfonic acid, and mixtures thereof.

19. The composition according to claim 16, in which the organic UVA-screening agents of the type (B) are chosen from benzophenone compounds; phenylbenzotriazole compounds; methylenebis(hydroxyphenylbenzotriazole) compounds; bis-resorcinyl triazine compounds; benzoxazole compounds; symmetrical triazines substituted with naphthalenyl or polyphenyl groups; and mixtures thereof.

20. The composition according to claim 19, in which the organic UVA-screening agents of the type (B) are chosen from the following compounds:

Drometrizole Trisiloxane,

Methylenebis(benzotriazolyl)tetramethylbutylphenol in the form of an aqueous dispersion of micronized particles, Bis(ethylhexyloxyphenol)methoxyphenyltriazine, Benzophenone-3, 2,4,6-Tris(diphenyl)triazine in micronized form, and mixtures thereof.

21. A non-therapeutic cosmetic process for caring for and/or making up a keratin material, comprising the application, to the surface of the said keratin material, of at least one composition as defined in claim 4.

22. A non-therapeutic cosmetic process for limiting the darkening of the skin and/or improving the colour and/or the uniformity of the complexion, comprising the application, to the surface of the skin, of at least one composition as defined in claim 4.

23. A non-therapeutic cosmetic process for preventing and/or treating the signs of ageing of a keratin material, comprising the application, to the surface of the keratin material, of at least one composition as defined in claim 4.

24. The composition according to claim 4, comprises:
0.2% to 5% by weight relative to the total weight of the composition of the at least one merocyanine compound of formula (1);
at least one organic UVB-screening agent chosen from:
    v) 0.2% to 25% by weight relative to the total weight of the composition of a liquid lipophilic organic UVB-screening agent
    vi) 0.2% to 10% by weight relative to the total weight of the composition of a hydrophilic organic UVB-screening agent
    vii) 0.2% to 20% by weight relative to the total weight of the composition of a triazine UVB-screening agent and
    iv) mixtures thereof;
and when present 0.01% to 30% by weight relative to the total weight of the composition of at least one organic UVA-screening agent other than the said merocyanine compound in the composition.

25. The composition according to claim 24, wherein the amount of the liquid lipophilic organic UVB-screening agent when present is 0.5% to 15% by weight relative to the total weight of the composition; the amount of the triazine UVB-screening agent when present is 0.5% to 10% by weight relative to the total weight of the composition and the amount of the at least one organic UVA-screening agent other than the said merocyanine compound when present is 0.1% to 15% by weight relative to the total weight of the composition.

26. The composition according to claim 4, wherein the oily phase comprises at least one oil selected from the group of hydrocarbon-based oils, silicon oils and fluoro oils.

27. The composition according to claim 26, wherein the amount of the oily phase is 5 to 95% by weight relative to the total weight of the composition.

28. The composition according to claim 26, wherein the amount of the oily phase is 10 to 80% by weight relative to the total weight of the composition.

29. The composition according to claim 4, wherein the amount of the oily phase is 5 to 95% by weight relative to the total weight of the composition.

30. The composition according to claim 4, wherein the amount of the oily phase is 10 to 80% by weight relative to the total weight of the composition.

\* \* \* \* \*